12) United States Patent
Törjék et al.

(10) Patent No.: US 11,434,499 B2
(45) Date of Patent: Sep. 6, 2022

(54) RESISTANCE GENE TO RHIZOMANIA

(71) Applicant: KWS SAAT SE & Co. KGaA, Einbeck (DE)

(72) Inventors: Ottó Törjék, Einbeck (DE); Dietrich Borchardt, Einbeck (DE); Wolfgang Mechelke, Einbeck (DE); Jens Christoph Lein, Gottingen (DE); Sandra Habekost, Dassel (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

(21) Appl. No.: 16/323,884

(22) PCT Filed: Aug. 10, 2017

(86) PCT No.: PCT/EP2017/070334
§ 371 (c)(1),
(2) Date: May 30, 2019

(87) PCT Pub. No.: WO2018/029300
PCT Pub. Date: Feb. 15, 2018

(65) Prior Publication Data
US 2019/0284570 A1 Sep. 19, 2019

(30) Foreign Application Priority Data
Aug. 10, 2016 (EP) .................................... 16183533

(51) Int. Cl.
C12N 15/82 (2006.01)
C07K 14/415 (2006.01)
C12Q 1/6895 (2018.01)

(52) U.S. Cl.
CPC ........ *C12N 15/8279* (2013.01); *C07K 14/415* (2013.01); *C12N 15/8283* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| 10,017,781 B2 | 7/2018 | Torjek et al. |
| 2016/0152999 A1 | 6/2016 | Torjek et al. |

FOREIGN PATENT DOCUMENTS

| DE | 10 2012 022 178 A1 | 5/2014 |
| DE | 10 2013 101 617 A1 | 8/2014 |
| DE | 10 2013 010 026 A1 | 12/2014 |
| WO | 00/29592 | 5/2000 |
| WO | 2006/128444 | 12/2006 |
| WO | 2007/147395 | 12/2007 |
| WO | 2011/032537 A1 | 3/2011 |
| WO | 2013/050024 | 4/2013 |
| WO | 2013/091612 | 6/2013 |
| WO | 2013/127379 A1 | 9/2013 |
| WO | 2014/144155 A1 | 9/2014 |
| WO | 2014202044 A1 | 12/2014 |

OTHER PUBLICATIONS

Grimmer et al., Theor Appl Genet 114: 1151-1160, 2007 (Year: 2007) provided in IDS.*
Odell et al., "Identification of DNA sequences required for activity of the cauliflower mosaic virus 35S promoter", Nature, 1985, vol. 313, pp. 810-812.
Rushton et al., "Interaction of elicitor-induced DNA-binding proteins with elicitor response elements in the promoters of parsley PR1 genes", The EMBO Journal, 1996, vol. 15, No. 20, pp. 5690-5700.
Osakabe et al., "Genome Editing with Engineered Nucleases in Plants", Plant & Cell Physiology, 2015, vol. 56, No. 3, pp. 389-400.
Henikoff et al., "Tilling. Traditional Mutagenesis Meets Functional Genomics", Plant Physiology, 2004, vol. 135, pp. 630-636.
Clark et al., "Characteristics of the Microplate Method of Enzyme-Linked Immunosorbent Assay for the Detection of Plant Viruses", J. Gen. Virol., 1977, vol. 34, pp. 475-483.
Martin et al., "Understanding the Functions of Plant Disease Resistance Proteins", Annual Review Plant Biology, 2003, vol. 54, pp. 23-61.
Lindsey et al., "Transformation of Sugarbeet (*Beta vulgaris*) by Agrobacterium tumefaciens". Journal of Experimental Botany, 1990, vol. 41, No. 226, pp. 529-536.
Database EMBL [Online] "*Beta vulgaris* subsp. *vulgaris* hypothetical protein", Jul. 8, 2015, retrieved from EBI accession No. KMT15745.
Scholten O.E. et al., "Inheritance of resistance to beet necrotic yellow vein virus in Beta vulgaris conferred by a second gene for resistance", Theoretical and Applied Genetics; International Journal of Plant Breeding Research, Springer Berlin, DE, vol. 99, No. 3-4, Aug. 1, 1999, pp. 740-746.
Amiri R. et al., "A new RAPD marker for beet necrotic yellow vein virus resistance gene in Beta vulgaris", Biologia Plantarum, Kluwer Academic Publishers, DO, vol. 53, No. 1, Mar. 21, 2009, pp. 112-119.
Grimmer M.K. et al., "An anchored linkage map for sugar beet based on AFLP, SNP and RAPD markers and QTL mapping of a new source of resistance to Beet necrotic yellow vein virus", Theoretical and Applied Genetics; International Journal of Plant Breeding Research, Springer, Berlin, DE, vol. 114, No. 7, Feb. 9, 2007, pp. 1151-1160.

(Continued)

Primary Examiner — Elizabeth F McElwain
(74) Attorney, Agent, or Firm — Troutman Pepper Hamilton Sanders LLP

(57) ABSTRACT

The invention relates to nucleic acid molecules which impart resistance to rhizomania, in particular to Beet Necrotic Yellow Vein Virus (BNYVV) in a plant, in particular of the genus *Beta*, and to plants containing such nucleic acid molecules. The invention further relates to methods for producing such BNYVV resistant plants and to marker-based methods for identifying and selecting BNYVV resistant plants, as well as to methods for controlling infection with the pathogen BNYVV.

4 Claims, 2 Drawing Sheets
Specification includes a Sequence Listing.

(56) References Cited

OTHER PUBLICATIONS

International Search Report dated May 10, 2017, issued in corresponding European Patent Application No. PCT/EP2017/070334.
Lein et al., "Resistance gene analogues are clustered on chromosome 3 of sugar beet and cosegregate with QTL for rhizomania resistance", Genome, 2007, vol. 50, No. 1, pp. 61-71.

* cited by examiner

A (SEQ ID NO: 1)

ATGGAAGCATTTCAGTCTGACATCGCGTTGGCTTTGCTTCAAGATTTGTTAGAAAGATTTAAATCATTAGTCATTGATGA
AGCAGGTCAAATAGTACAGTTTGATGCAGAGGATGAACTGAAGAAACTGGAGAGGAAGCTATTAAAGGCCCAAGTCTTGC
TTGGCAGCTTTCAGCTGACAACCGACAAAAATTGGCAACACTGGGTTGGTGATGTCACCAGAGTTTGCTATGATGCTGAA
GACTTGGTTGATGATATAGTGCTTGATGCCGGCAAAACTTCATTGCTTGAGAAGATCTTGTCATATTTCACAAGAGGAAG
CATGGCCCGGAAGATCCAAGAGCTCCAAGATAGGTTGGAAGATATAATAAGTGGATTAGACATGGTTAACAAAACAAAGC
AACGAGCACAGCAATGTTATTAGGGGAGTTTGTTTATGGTAACGAACAATTACTCCTAACAGAGAAGTTATTTGGGAGG
GATGCAGATAAGGAGAACATTATCTCGATGTTACTGGAACAGACAATAAGCTCAGTATCTATTGTTGGCATGGACGGGCT
TGGTAAAACAACACTTGCTCAGAATATGCTATATGATTCCAGAATCCAGGAGAAATTTCATCATAGAGTGTGGGTCCGTG
TGTCTGCGAAGTTTGATCTGAGAAAAATCACAGACTTTATCTTACATCGCAGGCAGGAATGTGAGTACAGCTTTCTTCCT
GAGAAAATATATGGTTTGTTTCACGATCTGTATATGGGTAAAAGTATATTGATTGTGTTGGATGACTTATGGGATGTGAA
GTACGATGATTGGAGGTCTTTTCGCTCTTTGTTTCTGCGCTCTTCTGGTTGCAAAGTTCTTCTCACCACTAGCAATCCAA
ATGTAACAACGGTTACAAAAGCTACACCGTATCATTTAAAATTGATGAAGGATGAAGATTGCCAAGCTCTAATCATGGAT
AGAGTTTTCTCATCTAATAATCTATCTGAACGTCAGCTTGTAATCTTGGAGGATATTGCTGTAGCAGTTGCCCAAAAGTG
CAAGGGCTTGCCTCTGGCAGCCAATGTTTTGGGCCTCCATTTATCTTCTGGGCGTAGAGATGATGAATGGATGAATTTTT
TAGATAGAGACATATGCGAGTTGAGGGTATTCAAAGAAGAAATATTTCCTGCTTTTAGACTGAACAACCCTTGTTTGGCA
TCACACTTAAAGAAGTGTCTTGCTTACTGCTCATTATTTCCTCATGATTACGATTTCAAGAAAGAAAACTTAGTTCAGCT
ATGGATGTCAGAAGGTTTTTTTCTGCCTCAAAGGATGACAAGCCTAGAACAAATTGGCAGTGATTGTTTTGATGAGCTCT
TGTGGAGATCTGTCTTTCAACTTTCACATGTTGGTGATCAGGAGCTACCAACTTACAAAATGCATGAATTTATTCGCAGG
TTTGCTGAATTTGTGGCCTCAGACACATGTTTCCGGTGGGAGGAAGGTCAGAGCTCTTTCTCAGTTCCTTGGTACAAAAC
GGCTCGTCATTTATCTTTGCTTTGTGATTGCATCAAACCAGCATTCCTTAAATACATTGAAAATTGTGATGGTCTGAGGA
CATTTCTTCTGCTAAGTGAAAAAGGAACACAAATTGGCCAGCTTCCTTATTCACTTTTCCAGAAACTAGTACGACTGCGA
GTTCTGGACTTGAGTCGTACTGATATTGATGAGCTCCCGGAGTCATTGGGTAGATTAAAGTATCTTCGGTATTTCGATGC
ATCTCAGACACATATCCTAAGGTTGCCTAAGTCAGTGACCAACCTTCATCAATTACAAGTACTCAGATTGAGAGAATGTT
ATAAACTTCTAGAGTTGCCAAAAAACATTAAGAACCTGACTAACCTTCTACATCTTGACGTGGACATTAAAGGATTGAGG
TGTAGGCCAGCAAGTATAGGAAGTCTAAGTTGCCTTAAAACACTTCCTTCCTTTGCTGTTTGTAAGAAGGTAGGATATCG
CATTGCAGAGTTGAAGAATCTGAAGAATCTATGTGGTACAATTTGCCTTAGTAATCTTGAAAATGTTAAGGATGGGGCAG
AGGCCAGGGACGCGATGATATGTGATAAGCCATATATCAAAAGGTTGGAATTAGAATGGAGCCGTTTTTCTCGAGATGGG
TCAATAGAGATGGATGTTCTTGCTGGCCTTCAACCAGACAAAAATTTGAAAGAACTGCAAGTAATCAACTATGGTGGTTC
GAGCTTTCCTGCTTGGCTTACAAGCCCATCTTGCATGCTTGTGAGTATCTATATGCAAAATTGTCGGCAAGATGACTTTC
TGCCTTCACTTGGGCAACTTCCTTTCCTCAAGACACTTCATGTTGAAGGTATGCATAGCGTGAAGTATGTGGACTATCAT
TTTTGTGGTGAAAGTACAACTGGGGCCTTTCCTTCCTTGGAATCACTGAAGATCCAGGACATGATGTGCCTTATGAGTTG
GTATCCATTACCAGACAATAGCTTGCTCCAACTCCGTGATCTTACAATAGAGGATTGTCCAAGTCTCTTCTCAATGCAAT
CGCTAAAACATATGAGTTCACTACAAGAACTAGTGATCAACTGTTGCCCAGGGCTGGAGACATTGCCTCAGCTACCAGGA
TCAATTCAGTCATTGATCATTTTCGAAAGTGATATGGTGAAACAGCGGTGTCAGATTGAAGAAGGTCCTGAATGGAACAT
CATAAAAACAATTCCTTATGTGGAGATTGACTACGAGAGTATGTTTCCTGGAGATTCAAGTTAG

B (SEQ ID NO: 2)

MEAFQSDIALALLQDLLERFKSLVIDEAGQIVQFDAEDELKKLERKLLKAQVLLGSFQLTTDKNWQHWVGDVTRVCYDAE
DLVDDIVLDAGKTSLLEKILSYFTRGSMARKIQELQDRLEDIISGLDMVNKTKQRAQQCYLGEFVYGNEQLLLTEKLFGR
DADKENIISMLLEQTISSVSIVGMDGLGKTTLAQNMLYDSRIQEKFHHRVWVRVSAKFDLRKITDFILHRRQECEYSFLP
EKIYGLFHDLYMGKSILIVLDDLWDVKYDDWRSFRSLFLRSSGCKVLLTTSNPNVTTVTKATPYHLKLMKDEDCQALIMD
RVFSSNNLSERQLVILEDIAVAVAQKCKGLPLAANVLGLHLSSGRRDDEWMNFLDRDICELRVFKEEIFPAFRLNNPCLA
SHLKKCLAYCSLFPHDYDFKKENLVQLWMSEGFFLPQRMTSLEQIGSDCFDELLWRSVFQLSHVGDQELPTYKMHEFIRR
FAEFVASDTCFRWEEGQSSFSVPWYKIARHLSLLCDCIKPAFLKYIENCDGLRTFLLLSEKGTQIGQLPYSLFQKLVRLR
VLDLSRTDIDELPESLGRLKYLRYFDASQTHILRLPKSVTNLHQLQVLRLRECYKLLELPKNIKNLTNLLHLDVDIKGLR
CRPASIGSLSCLKTLPSFAVCKKVGYRIAELKNLKNLCGTICLSNLENVKDGAEARDAMICDKPYIKRLELEWSRFSRDG
SIEMDVLAGLQPDKNLKELQVINYGGSSFPAWLTSPSCMLVSIYMQNCRQDDFLPSLGQLPFLKTLHVEGMHSVKYVDYH
FCGESTTGAFPSLESLKIQDMMCLMSWYPLPDNSLLQLRDLTIEDCPSLFSMQSLKHMSSLQELVINCCPGLETLPQLPG
SIQSLIIFESDMVKQRCQIEEGPEWNIIKTIPYVEIDYESMFPGDSS*

C (SEQ ID NO: 3)

```
ATGGAAGCATTTCAGTCTGACATCGCGTTGGCTTTGCTTCAAGATTTGTTAGAAAGATTTAAATCATTAGTCATCGATGA
AGCAGGTCAAGTAGTACAGTTTGATGCAGAGGATGAACTGAAGAAACTGGAGAGGAAGCTAAAAAAGGCCCAAGTCTTGC
TTGGCAGCTTTCAGCTGACAACCGACAAAAATTGGCAACACTGGGTTGGTGATGTCACCAGAGTTTGCTATGATGCTGAG
GACTTGGTTGATGATATAGTGCTTGATGCCGGCAAAACTTCATTGCTTGAGAAGATCTTGTCATATTTCACAAGAGGAAG
CATGGCCCGGAAGATCCAAGAGCTCCAAGATAGGTTGGAAGATATAATAAGTGGATTAGACATGGTTAACAAAACAAAGC
AACGAGCACAGCAATGTTATTTAGGGGAGTTTGTTTATGGTAACGAACAATTACTCCTAACAGAGAAGTTATTTGGGAGG
GATGCAGATAAGGAGAACATTATCACGATGTTGCTGGAACAGACAATAAGCTCAGTATCTATTGTTGGCATGGACGGGCT
TGGTAAAACAACACTTGCTCAGAATATACTATATGATTCCAGAATCCAGGAGAAATTTCATCATAGAGTGTGGGTCCGTG
TGTCTGCGAAGTTTGATCTGAGAAAAATCACAGACTTTATCTTACATCGCAGGCAGGAATGTGAGTACAGCTTTCTTCCT
GAGAAAATACATTGTTTGTTTCACGATCTGTATATGGGTAAAAGTATATTGATTGTGTTGGATGACTTATGGGATGTGAA
GTACAATGATTGGAGCTCTTTTCGCTCTTTGTTTCTGCGCTCTTCTGGTTGCAAAGTTCTTCTCACCACTAGCAATCCAA
ATGTAACAACGGTTACAAAAGCTACTCCGTATCATTTACAATTGATGAAGGATGAAGATTGCCAAGCTCTAATCATGGAT
AGAGTTTTCTCATCTAATAATCTATCTGAACGTCAGCTTGTAATCTTGGAGGATATTGCTGTAGCAGTTGCCCAAAAGTG
CAAGGGCTTGCCTCTGGCAGCCAATGTTTTGGGCCTCCATTTATCTTCTGGGCGTAGAGATGATGAATGGATGAATTTTT
TAGATAGAGACATATGTGAGTTGAGGGTATTCAAAGAAGAAATATTTCCTGCTTTTAGACTGAACAACCCTGGTTTGGCA
TCACACTTAAAGAAGTGTCTTGCTTACTGCTCATTATTTCCTCATGATTACGATTTCAAGAAAGAAAACTTAGTTCAGCT
ATGGATGTCAGAAGGTTTTTTTCTGCCTCGAAGGATGACAAGCCTAGAACAAATTGGCAGTGATTGTTTTGATGAGCTCT
TGTGGAGATCTGTCTTTCAACTTTCACATGTTGGTGATCAGGAGCTACCAACTTACAAAATGCATGAATTTATTCGCAGG
TTTGCTGAATTTGTGGCCTCAGACACATGTTTCCGGTGGGAGGAAGGTCAGAGCTCTTTCTCAGTTCCTTGGTACAAAAC
GGCTCGTCATTTATCTTTGCTTTGTGATTGCATCAAACCAGCATTCCTTAAATACATTGAAAATTGTGATGGTCTTAGGA
CATTTCTTCTGCTAAGTGAAAAAGGAACACAAATTGGCCAGCTTCCTTATTCACTTTTCCAGAAACTAGTACGACTGCGA
GTTCTGGACTTGAGTCATACTGATATTGATGAGCTCCCGGAGTCATTGGGTAGATTAAAGTATCTTCGGTATTTCGATGC
ATCTCAGACACATATCCTAAGGTTGCCTAAGTCAGTGACCAACCTTCATCAATTACAAGTACTCAGATTGAGAGAATGTT
ATAAACTTCTAGAGTTGCCAAAAAACATTAAGAACCTGACTAACCTTCTACATCTTGACGTGGACATTAAAGGATTGAGG
TGTAGGCCAGCAAGTATAGGAAGTCTAAGTTGCCTTAAAACACTTCCTTCCTTTGCTGTTTGTAAGAAGGTAGGATATCG
CATTGCAGAGTTGAAGAATCTGAAGAATCTATGTGGTACAATTTGCCTTAGTAATCTTGAAAATGTTAAGGATGGGGCAG
AGGCCAGGGACGCGATGATATGTGATAAGCCATATATCAAAAGGTTGGAATTAGAATGGAGCCGTTTTTCTCGAGATGGG
TCAATAGAGATGGATGTCCTTGCTGGCCTTAAACCAGACAAAAATTTGAAAGAACTGCAAGTAATCAATTATGGTGGTTC
GAGCTTTCCTGCTTGGCTTACAAGCCCATCTTGCATGCTTGTGAGTATCTATATGCAAAACTGTCGGCAAGATGACTTTC
TGCCTTCGCTTGGGCAACTTCCTTTCCTCAAGACACTTCATGTTGAAGGTATGCATAGCGTGAAGTATGTGGACTATCAT
TTTTGTGGTGAAAGTACAACTGGGGCCTTTCCTTCCTTGGAATCACTGAAGATCCAGGACATGATGTGCCTTATGAGTTG
GTATCCATTATCAGACAATAGCTTGCTCCAGCTCCGTGATCTACAATTGAGGATTGTCCAAGTCTCTTCTCAATGCAAT
CGCTAAAACATATGAGTTCACTACAAGAACTAGTGATCAACTGTTGCCCAGGGCTGGAGACATTGCCTCAGCTACCAGGA
TCAGTTCAGTCATTGATCATTTTCGGAAGTGATATGGTGAAACAGCGGTGTCAGATTGAAGAAGGTCCTGAATGGAACAT
GATAAAAACAATTCCTTATGTGGAGATTGACTACGAGAGTATGTTTCCTGGAGATTCAAGTTAG
```

D (SEQ ID NO: 4)

```
MEAFQSDIALALLQDLLERFKSLVIDEAGQVVQFDAEDELKKLERKLKKAQVLLGSFQLTTDKNWQHWVGDVTRVCYDAE
DLVDDIVLDAGKTSLLEKILSYFTRGSMARKIQELQDRLEDIISGLDMVNKTKQRAQQCYLGEFVYGNEQLLLTEKLFGR
DADKENIITMLLEQTISSVSIVGMDGLGKTTLAQNILYDSRIQEKFHHRVWVRVSAKFDLRKITDFILHRRQECEYSFLP
EKIHCLFHDLYMGKSILIVLDDLWDVKYNDWSSFRSLFLRSSGCKVLLTTSNPNVTTVTKATPYHLQLMKDEDCQALIMD
RVFSSNNLSERQLVILEDIAVAVAQKCKGLPLAANVLGLHLSSGRRDDEWMNFLDRDICELRVFKEEIFPAFRLNNPGLA
SHLKKCLAYCSLFPHDYDFKKENLVQLWMSEGFFLPRRMTSLEQIGSDCFDELLWRSVFQLSHVGDQELPTYKMHEFIRR
FAEFVASDTCFRWEEGQSSFSVPWYKTARHLSLLCDCIKPAFLKYIENCDGLRTFLLLSEKGTQIGQLPYSLFQKLVRLR
VLDLSHTDIDELPESLGRLKYLRYFDASQTHILRLPKSVTNLHQLQVLRLRECYKLLELPKNIKNLTNLLHLDVDIKGLR
CRPASIGSLSCLKTLPSFAVCKKVGYRIAELKNLKNLCGTICLSNLENVKDGAEARDAMICDKPYIKRLELEWSRFSRDG
SIEMDVLAGLKPDKNLKELQVINYGGSSFPAWLTSPSCMLVSIYMQNCRQDDFLPSLGQLPFLKTLHVEGMHSVKYVDYH
FCGESTTGAFPSLESLKIQDMMCLMSWYPLSDNSLLQLRDLTIEDCPSLFSMQSLKHMSSLQELVINCCPGLETLPQLPG
SVQSLIIFGSDMVKQRCQIEEGPEWNMIKTIPYVEIDYESMFPGDSS*
```

(Cont.)

SEQUENCE LISTING

<160> NUMBER OF SEQ ID NOS: 6

<210> SEQ ID NO 1
<211> LENGTH: 2784
<212> TYPE: DNA
<213> ORGANISM: Beta vulgaris subsp. vulgaris

<400> SEQUENCE: 1
atggaagcat ttcagtctga catcgcgttg gctttgcttc aagatttgtt agaaagattt 60
aaatcattag tcattgatga agcaggtcaa atagtacagt ttgatgcaga ggatgaactg 120
aagaaactgg agaggaagct attaaaggcc caagtcttgc ttggcagctt tcagctgaca 180
accgacaaaa attggcaaca ctgggttggt gatgtcacca gagtttgcta tgatgctgaa 240
gacttggttg atgatatagt gcttgatgcc ggcaaaactt cattgcttga gaagatcttg 300
tcatatttca caagaggaag catggcccgg aagatccaag agctccaaga taggttggaa 360
gatataataa gtggattaga catggttaac aaaacaaagc aacgagcaca gcaatgttat 420
ttaggggagt ttgtttatgg taacgaacaa ttactcctaa cagagaagtt atttgggagg 480
gatgcagata aggagaacat tatctcgatg ttactggaac agacaataag ctcagtatct 540
attgttggca tggacgggct tggtaaaaca acacttgctc agaatatgct atatgattcc 600
agaatccagg agaaatttca tcatagagtg tgggtccgtg tgtctgcgaa gtttgatctg 660
agaaaaatca cagactttat cttacatcgc aggcaggaat gtgagtacag ctttcttcct 720
gagaaaatat atggtttgtt tcacgatctg tatatgggta aaagtatatt gattgtgttg 780
gatgacttat gggatgtgaa gtacgatgat tggaggtctt ttcgctcttt gtttctgcgc 840
tcttctggtt gcaaagttct tctcaccact agcaatccaa atgtaacaac ggttacaaaa 900
gctacaccgt atcatttaaa attgatgaag gatgaagatt gccaagctct aatcatggat 960
agagttttct catctaataa tctatctgaa cgtcagcttg taatcttgga ggatattgct 1020
gtagcagttg cccaaaagtg caagggcttg cctctggcag ccaatgtttt gggcctccat 1080
ttatcttctg ggcgtagaga tgatgaatgg atgaattttt tagatagaga catatgcgag 1140
ttgagggtat tcaaagaaga aatatttcct gcttttagac tgaacaaccc ttgtttggca 1200
tcacacttaa agaagtgtct tgcttactgc tcattatttc ctcatgatta cgatttcaag 1260
aaagaaaact tagttcagct atggatgtca gaaggttttt ttctgcctca aaggatgaca 1320
agcctagaac aaattggcag tgattgtttt gatgagctct tgtggagatc tgtctttcaa 1380
ctttcacatg ttggtgatca ggagctacca acttacaaaa tgcatgaatt tattcgcagg 1440

```
tttgctgaat tgtggcctc agacacatgt ttccggtggg aggaaggtca gagctctttc    1500
tcagttcctt ggtacaaaac ggctcgtcat ttatctttgc tttgtgattg catcaaacca    1560
gcattcctta aatacattga aaattgtgat ggtctgagga catttcttct gctaagtgaa    1620
aaaggaacac aaattggcca gcttccttat tcacttttcc agaaactagt acgactgcga    1680
gttctggact tgagtcgtac tgatattgat gagctcccgg agtcattggg tagattaaag    1740
tatcttcggt atttcgatgc atctcagaca catatcctaa ggttgcctaa gtcagtgacc    1800
aaccttcatc aattacaagt actcagattg agagaatgtt ataaacttct agagttgcca    1860
aaaaacatta agaacctgac taaccttcta catcttgacg tggacattaa aggattgagg    1920
tgtaggccag caagtatagg aagtctaagt tgccttaaaa cacttccttc ctttgctgtt    1980
tgtaagaagg taggatatcg cattgcagag ttgaagaatc tgaagaatct atgtggtaca    2040
atttgcctta gtaatcttga aaatgttaag gatggggcag aggccaggga cgcgatgata    2100
tgtgataagc catatatcaa aaggttggaa ttagaatgga gccgtttttc tcgagatggg    2160
tcaatagaga tggatgttct tgctggcctt caaccagaca aaaatttgaa agaactgcaa    2220
gtaatcaact atggtggttc gagctttcct gcttggctta caagcccatc ttgcatgctt    2280
gtgagtatct atatgcaaaa ttgtcggcaa gatgactttc tgccttcact tgggcaactt    2340
cctttcctca agacacttca tgttgaaggt atgcatagcg tgaagtatgt ggactatcat    2400
ttttgtggtg aaagtacaac tggggccttt ccttccttgg aatcactgaa gatccaggac    2460
atgatgtgcc ttatgagttg gtatccatta ccagacaata gcttgctcca actccgtgat    2520
cttacaatag aggattgtcc aagtctcttc tcaatgcaat cgctaaaaca tatgagttca    2580
ctacaagaac tagtgatcaa ctgttgccca gggctggaga cattgcctca gctaccagga    2640
tcaattcagt cattgatcat tttcgaaagt gatatggtga acagcggtg tcagattgaa     2700 gaaggtcctg aatggaacat cataaaaaca attccttatg tggagattga ctacgagagt    2760
atgtttcctg gagattcaag ttag                                          2784
```

<210> SEQ ID NO 2
<211> LENGTH: 927
<212> TYPE: PRT
<213> ORGANISM: Beta vulgaris subsp. vulgaris

<400> SEQUENCE: 2

```
Met Glu Ala Phe Gln Ser Asp Ile Ala Leu Ala Leu Leu Gln Asp Leu
1               5                   10                  15

Leu Glu Arg Phe Lys Ser Leu Val Ile Asp Glu Ala Gly Gln Ile Val
            20                  25                  30

Gln Phe Asp Ala Glu Asp Glu Leu Lys Lys Leu Glu Arg Lys Leu Leu
        35                  40                  45

Lys Ala Gln Val Leu Leu Gly Ser Phe Gln Leu Thr Thr Asp Lys Asn
    50                  55                  60

Trp Gln His Trp Val Gly Asp Val Thr Arg Val Cys Tyr Asp Ala Glu
65                  70                  75                  80

Asp Leu Val Asp Asp Ile Val Leu Asp Ala Gly Lys Thr Ser Leu Leu
                85                  90                  95

Glu Lys Ile Leu Ser Tyr Phe Thr Arg Gly Ser Met Ala Arg Lys Ile
            100                 105                 110

Gln Glu Leu Gln Asp Arg Leu Glu Asp Ile Ile Ser Gly Leu Asp Met
        115                 120                 125
```

-continued

```
Val Asn Lys Thr Lys Gln Arg Ala Gln Gln Cys Tyr Leu Gly Glu Phe
130                 135                 140

Val Tyr Gly Asn Glu Gln Leu Leu Thr Glu Lys Leu Phe Gly Arg
145                 150                 155                 160

Asp Ala Asp Lys Glu Asn Ile Ile Ser Met Leu Leu Glu Gln Thr Ile
                165                 170                 175

Ser Ser Val Ser Ile Val Gly Met Asp Gly Leu Gly Lys Thr Thr Leu
            180                 185                 190

Ala Gln Asn Met Leu Tyr Asp Ser Arg Ile Gln Glu Lys Phe His His
        195                 200                 205

Arg Val Trp Val Arg Val Ser Ala Lys Phe Asp Leu Arg Lys Ile Thr
    210                 215                 220

Asp Phe Ile Leu His Arg Arg Gln Glu Cys Glu Tyr Ser Phe Leu Pro
225                 230                 235                 240

Glu Lys Ile Tyr Gly Leu Phe His Asp Leu Tyr Met Gly Lys Ser Ile
                245                 250                 255

Leu Ile Val Leu Asp Asp Leu Trp Asp Val Lys Tyr Asp Asp Trp Arg
            260                 265                 270

Ser Phe Arg Ser Leu Phe Leu Arg Ser Ser Gly Cys Lys Val Leu Leu
        275                 280                 285

Thr Thr Ser Asn Pro Asn Val Thr Thr Val Thr Lys Ala Thr Pro Tyr
    290                 295                 300

His Leu Lys Leu Met Lys Asp Glu Asp Cys Gln Ala Leu Ile Met Asp
305                 310                 315                 320

Arg Val Phe Ser Ser Asn Asn Leu Ser Glu Arg Gln Leu Val Ile Leu
                325                 330                 335

Glu Asp Ile Ala Val Ala Val Ala Gln Lys Cys Lys Gly Leu Pro Leu
            340                 345                 350

Ala Ala Asn Val Leu Gly Leu His Leu Ser Ser Gly Arg Arg Asp Asp
        355                 360                 365

Glu Trp Met Asn Phe Leu Asp Arg Asp Ile Cys Glu Leu Arg Val Phe
    370                 375                 380

Lys Glu Glu Ile Phe Pro Ala Phe Arg Leu Asn Asn Pro Cys Leu Ala
385                 390                 395                 400

Ser His Leu Lys Lys Cys Leu Ala Tyr Cys Ser Leu Phe Pro His Asp
                405                 410                 415

Tyr Asp Phe Lys Lys Glu Asn Leu Val Gln Leu Trp Met Ser Glu Gly
            420                 425                 430

Phe Phe Leu Pro Gln Arg Met Thr Ser Leu Glu Gln Ile Gly Ser Asp
        435                 440                 445

Cys Phe Asp Glu Leu Leu Trp Arg Ser Val Phe Gln Leu Ser His Val
450                 455                 460

Gly Asp Gln Glu Leu Pro Thr Tyr Lys Met His Glu Phe Ile Arg Arg
465                 470                 475                 480

Phe Ala Glu Phe Val Ala Ser Asp Thr Cys Phe Arg Trp Glu Glu Gly
                485                 490                 495

Gln Ser Ser Phe Ser Val Pro Trp Tyr Lys Thr Ala Arg His Leu Ser
            500                 505                 510

Leu Leu Cys Asp Cys Ile Lys Pro Ala Phe Leu Lys Tyr Ile Glu Asn
        515                 520                 525

Cys Asp Gly Leu Arg Thr Phe Leu Leu Ser Glu Lys Gly Thr Gln
    530                 535                 540

Ile Gly Gln Leu Pro Tyr Ser Leu Phe Gln Lys Leu Val Arg Leu Arg
```

|   |   |   |   |   | 545 |   |   |   |   | 550 |   |   |   |   | 555 |   |   |   |   | 560 |
|---|---|---|---|---|---|---|---|---|---|---|---|---|---|---|---|---|---|---|---|---|

Val Leu Asp Leu Ser Arg Thr Asp Ile Asp Glu Leu Pro Glu Ser Leu
            565                 570                 575

Gly Arg Leu Lys Tyr Leu Arg Tyr Phe Asp Ala Ser Gln Thr His Ile
            580                 585                 590

Leu Arg Leu Pro Lys Ser Val Thr Asn Leu His Gln Leu Gln Val Leu
            595                 600                 605

Arg Leu Arg Glu Cys Tyr Lys Leu Leu Glu Leu Pro Lys Asn Ile Lys
610                 615                 620

Asn Leu Thr Asn Leu Leu His Leu Asp Val Asp Ile Lys Gly Leu Arg
625                 630                 635                 640

Cys Arg Pro Ala Ser Ile Gly Ser Leu Ser Cys Leu Lys Thr Leu Pro
            645                 650                 655

Ser Phe Ala Val Cys Lys Lys Val Gly Tyr Arg Ile Ala Glu Leu Lys
            660                 665                 670

Asn Leu Lys Asn Leu Cys Gly Thr Ile Cys Leu Ser Asn Leu Glu Asn
            675                 680                 685

Val Lys Asp Gly Ala Glu Ala Arg Asp Ala Met Ile Cys Asp Lys Pro
690                 695                 700

Tyr Ile Lys Arg Leu Glu Leu Glu Trp Ser Arg Phe Ser Arg Asp Gly
705                 710                 715                 720

Ser Ile Glu Met Asp Val Leu Ala Gly Leu Gln Pro Asp Lys Asn Leu
            725                 730                 735

Lys Glu Leu Gln Val Ile Asn Tyr Gly Gly Ser Ser Phe Pro Ala Trp
            740                 745                 750

Leu Thr Ser Pro Ser Cys Met Leu Val Ser Ile Tyr Met Gln Asn Cys
            755                 760                 765

Arg Gln Asp Asp Phe Leu Pro Ser Leu Gly Gln Leu Pro Phe Leu Lys
            770                 775                 780

Thr Leu His Val Glu Gly Met His Ser Val Lys Tyr Val Asp Tyr His
785                 790                 795                 800

Phe Cys Gly Glu Ser Thr Thr Gly Ala Phe Pro Ser Leu Glu Ser Leu
            805                 810                 815

Lys Ile Gln Asp Met Met Cys Leu Met Ser Trp Tyr Pro Leu Pro Asp
            820                 825                 830

Asn Ser Leu Leu Gln Leu Arg Asp Leu Thr Ile Glu Asp Cys Pro Ser
            835                 840                 845

Leu Phe Ser Met Gln Ser Leu Lys His Met Ser Ser Leu Gln Glu Leu
            850                 855                 860

Val Ile Asn Cys Cys Pro Gly Leu Glu Thr Leu Pro Gln Leu Pro Gly
865                 870                 875                 880

Ser Ile Gln Ser Leu Ile Ile Phe Glu Ser Asp Met Val Lys Gln Arg
            885                 890                 895

Cys Gln Ile Glu Glu Gly Pro Glu Trp Asn Ile Lys Thr Ile Pro
            900                 905                 910

Tyr Val Glu Ile Asp Tyr Glu Ser Met Phe Pro Gly Asp Ser Ser
            915                 920                 925

<210> SEQ ID NO 3
<211> LENGTH: 2784
<212> TYPE: DNA
<213> ORGANISM: Beta vulgaris subsp. maritima

<400> SEQUENCE: 3

```
atggaagcat ttcagtctga catcgcgttg gctttgcttc aagatttgtt agaaagattt      60
aaatcattag tcatcgatga agcaggtcaa gtagtacagt ttgatgcaga ggatgaactg     120
aagaaactgg agaggaagct aaaaaaggcc caagtcttgc ttggcagctt tcagctgaca     180
accgacaaaa attggcaaca ctgggttggt gatgtcacca gagtttgcta tgatgctgag     240
gacttggttg atgatatagt gcttgatgcc ggcaaaactt cattgcttga aagatcttg      300
tcatatttca aagaggaag catggcccgg aagatccaag agctccaaga taggttggaa      360
gatataataa gtggattaga catggttaac aaaacaaagc aacgagcaca gcaatgttat     420
ttaggggagt ttgtttatgg taacgaacaa ttactcctaa cagagaagtt atttgggagg     480
gatgcagata aggagaacat tatcacgatg ttgctggaac agacaataag ctcagtatct     540
attgttggca tggacgggct tggtaaaaca cacttgctc agaatatact atatgattcc      600
agaatccagg agaaatttca tcatagagtg tgggtccgtg tgtctgcgaa gtttgatctg     660
agaaaaatca cagactttat cttacatcgc aggcaggaat gtgagtacag ctttcttcct     720
gagaaaatac attgtttgtt tcacgatctg tatatgggta aaagtatatt gattgtgttg     780
gatgacttat gggatgtgaa gtacaatgat tggagctctt ttcgctcttt gtttctgcgc     840
tcttctggtt gcaaagttct tctcaccact agcaatccaa atgtaacaac ggttacaaaa     900
gctactccgt atcatttaca attgatgaag gatgaagatt gccaagctct aatcatggat     960
agagttttct catctaataa tctatctgaa cgtcagcttg taatcttgga ggatattgct    1020
gtagcagttg cccaaaagtg caagggcttg cctctggcag ccaatgtttt gggcctccat    1080
ttatcttctg gcgtagaga tgatgaatgg atgaattttt tagatagaga catatgtgag    1140
ttgagggtat tcaaagaaga aatatttcct gcttttagac tgaacaaccc tggtttggca    1200
tcacacttaa agaagtgtct tgcttactgc tcattatttc ctcatgatta cgatttcaag    1260
aaagaaaact tagttcagct atggatgtca gaaggttttt ttctgcctcg aaggatgaca    1320
agcctagaac aaattggcag tgattgtttt gatgagctct gtggagatc tgtcttcaa     1380
cttttcacatg ttggtgatca ggagctacca acttacaaaa tgcatgaatt tattcgcagg    1440
tttgctgaat tgtggcctc agacacatgt ttccggtggg aggaaggtca gagctctttc    1500
tcagttcctt ggtacaaaac ggctcgtcat ttatctttgc tttgtgattg catcaaacca    1560
gcattcctta atacattga aaattgtgat ggtcttagga catttcttct gctaagtgaa    1620
aaaggaacac aaattggcca gcttccttat tcactttttcc agaaactagt acgactgcga    1680
gttctggact tgagtcatac tgatattgat gagctcccgg agtcattggg tagattaaag    1740
tatcttcggt atttcgatgc atctcagaca catatcctaa ggttgcctaa gtcagtgacc    1800
aaccttcatc aattacaagt actcagattg agagaatgtt ataaacttct agagttgcca    1860
aaaaacatta gaacctgac taaccttcta catcttgacg tggacattaa aggattgagg    1920
tgtaggccag caagtatagg aagtctaagt tgccttaaaa cacttccttc ctttgctgtt    1980
tgtaagaagg taggatatcg cattgcagag ttgaagaatc tgaagaatct atgtggtaca    2040
atttgcctta gtaatcttga aaatgttaag gatggggcag aggccaggga cgcgatgata    2100
tgtgataagc catatatcaa aaggttggaa ttagaatgga gccgtttttc tcagatgggg    2160
tcaatagaga tggatgtcct tgctggcctt aaaccagaca aaaatttgaa agaactgcaa    2220
gtaatcaatt atggtggttc gagctttcct gcttggctta caagcccatc ttgcatgctt    2280
gtgagtatct atatgcaaaa ctgtcggcaa gatgactttc tgccttcgct tgggcaactt    2340
cctttcctca agacacttca tgttgaaggt atgcatagcg tgaagtatgt ggactatcat    2400
```

-continued

```
ttttgtggtg aaagtacaac tggggccttt ccttccttgg aatcactgaa gatccaggac    2460
atgatgtgcc ttatgagttg gtatccatta tcagacaata gcttgctcca gctccgtgat    2520
cttacaattg aggattgtcc aagtctcttc tcaatgcaat cgctaaaaca tatgagttca    2580
ctacaagaac tagtgatcaa ctgttgccca gggctggaga cattgcctca gctaccagga    2640
tcagttcagt cattgatcat tttcggaagt gatatggtga acagcggtg tcagattgaa     2700 gaaggtcctg aatggaacat gataaaaaca attccttatg tggagattga ctacgagagt    2760
atgtttcctg gagattcaag ttag                                            2784
```

<210> SEQ ID NO 4
<211> LENGTH: 927
<212> TYPE: PRT
<213> ORGANISM: Beta vulgaris subsp. maritima

<400> SEQUENCE: 4

```
Met Glu Ala Phe Gln Ser Asp Ile Ala Leu Ala Leu Leu Gln Asp Leu
1               5                   10                  15

Leu Glu Arg Phe Lys Ser Leu Val Ile Asp Glu Ala Gly Gln Val Val
            20                  25                  30

Gln Phe Asp Ala Glu Asp Glu Leu Lys Lys Leu Glu Arg Lys Leu Lys
        35                  40                  45

Lys Ala Gln Val Leu Leu Gly Ser Phe Gln Leu Thr Thr Asp Lys Asn
    50                  55                  60

Trp Gln His Trp Val Gly Asp Val Thr Arg Val Cys Tyr Asp Ala Glu
65                  70                  75                  80

Asp Leu Val Asp Asp Ile Val Leu Asp Ala Gly Lys Thr Ser Leu Leu
                85                  90                  95

Glu Lys Ile Leu Ser Tyr Phe Thr Arg Gly Ser Met Ala Arg Lys Ile
            100                 105                 110

Gln Glu Leu Gln Asp Arg Leu Glu Asp Ile Ile Ser Gly Leu Asp Met
        115                 120                 125

Val Asn Lys Thr Lys Gln Arg Ala Gln Gln Cys Tyr Leu Gly Glu Phe
    130                 135                 140

Val Tyr Gly Asn Glu Gln Leu Leu Leu Thr Glu Lys Leu Phe Gly Arg
145                 150                 155                 160

Asp Ala Asp Lys Glu Asn Ile Ile Thr Met Leu Leu Glu Gln Thr Ile
                165                 170                 175

Ser Ser Val Ser Ile Val Gly Met Asp Gly Leu Gly Lys Thr Thr Leu
            180                 185                 190

Ala Gln Asn Ile Leu Tyr Asp Ser Arg Ile Gln Glu Lys Phe His His
        195                 200                 205

Arg Val Trp Val Arg Val Ser Ala Lys Phe Asp Leu Arg Lys Ile Thr
    210                 215                 220

Asp Phe Ile Leu His Arg Arg Gln Glu Cys Glu Tyr Ser Phe Leu Pro
225                 230                 235                 240

Glu Lys Ile His Cys Leu Phe His Asp Leu Tyr Met Gly Lys Ser Ile
                245                 250                 255

Leu Ile Val Leu Asp Asp Leu Trp Asp Val Lys Tyr Asn Asp Trp Ser
            260                 265                 270

Ser Phe Arg Ser Leu Phe Leu Arg Ser Ser Gly Cys Lys Val Leu Leu
        275                 280                 285

Thr Thr Ser Asn Pro Asn Val Thr Val Thr Lys Ala Thr Pro Tyr
    290                 295                 300
```

```
His Leu Gln Leu Met Lys Asp Glu Asp Cys Gln Ala Leu Ile Met Asp
305                 310                 315                 320

Arg Val Phe Ser Ser Asn Asn Leu Ser Glu Arg Gln Leu Val Ile Leu
                325                 330                 335

Glu Asp Ile Ala Val Ala Val Ala Gln Lys Cys Lys Gly Leu Pro Leu
            340                 345                 350

Ala Ala Asn Val Leu Gly Leu His Leu Ser Ser Gly Arg Arg Asp Asp
        355                 360                 365

Glu Trp Met Asn Phe Leu Asp Arg Asp Ile Cys Glu Leu Arg Val Phe
    370                 375                 380

Lys Glu Glu Ile Phe Pro Ala Phe Arg Leu Asn Asn Pro Gly Leu Ala
385                 390                 395                 400

Ser His Leu Lys Lys Cys Leu Ala Tyr Cys Ser Leu Phe Pro His Asp
                405                 410                 415

Tyr Asp Phe Lys Lys Glu Asn Leu Val Gln Leu Trp Met Ser Glu Gly
            420                 425                 430

Phe Phe Leu Pro Arg Arg Met Thr Ser Leu Glu Gln Ile Gly Ser Asp
        435                 440                 445

Cys Phe Asp Glu Leu Leu Trp Arg Ser Val Phe Gln Leu Ser His Val
    450                 455                 460

Gly Asp Gln Glu Leu Pro Thr Tyr Lys Met His Glu Phe Ile Arg Arg
465                 470                 475                 480

Phe Ala Glu Phe Val Ala Ser Asp Thr Cys Phe Arg Trp Glu Glu Gly
                485                 490                 495

Gln Ser Ser Phe Ser Val Pro Trp Tyr Lys Thr Ala Arg His Leu Ser
            500                 505                 510

Leu Leu Cys Asp Cys Ile Lys Pro Ala Phe Leu Lys Tyr Ile Glu Asn
        515                 520                 525

Cys Asp Gly Leu Arg Thr Phe Leu Leu Leu Ser Glu Lys Gly Thr Gln
    530                 535                 540

Ile Gly Gln Leu Pro Tyr Ser Leu Phe Gln Lys Leu Val Arg Leu Arg
545                 550                 555                 560

Val Leu Asp Leu Ser His Thr Asp Ile Asp Glu Leu Pro Glu Ser Leu
                565                 570                 575

Gly Arg Leu Lys Tyr Leu Arg Tyr Phe Asp Ala Ser Gln Thr His Ile
            580                 585                 590

Leu Arg Leu Pro Lys Ser Val Thr Asn Leu His Gln Leu Gln Val Leu
        595                 600                 605

Arg Leu Arg Glu Cys Tyr Lys Leu Leu Glu Leu Pro Lys Asn Ile Lys
    610                 615                 620

Asn Leu Thr Asn Leu Leu His Leu Asp Val Asp Ile Lys Gly Leu Arg
625                 630                 635                 640

Cys Arg Pro Ala Ser Ile Gly Ser Leu Ser Cys Leu Lys Thr Leu Pro
                645                 650                 655

Ser Phe Ala Val Cys Lys Lys Val Gly Tyr Arg Ile Ala Glu Leu Lys
            660                 665                 670

Asn Leu Lys Asn Leu Cys Gly Thr Ile Cys Leu Ser Asn Leu Glu Asn
        675                 680                 685

Val Lys Asp Gly Ala Glu Ala Arg Asp Ala Met Ile Cys Asp Lys Pro
    690                 695                 700

Tyr Ile Lys Arg Leu Glu Leu Glu Trp Ser Arg Phe Ser Arg Asp Gly
705                 710                 715                 720
```

```
Ser Ile Glu Met Asp Val Leu Ala Gly Leu Lys Pro Asp Lys Asn Leu
            725                 730                 735

Lys Glu Leu Gln Val Ile Asn Tyr Gly Gly Ser Ser Phe Pro Ala Trp
        740                 745                 750

Leu Thr Ser Pro Ser Cys Met Leu Val Ser Ile Tyr Met Gln Asn Cys
    755                 760                 765

Arg Gln Asp Asp Phe Leu Pro Ser Leu Gly Leu Pro Phe Leu Lys
770                 775                 780

Thr Leu His Val Glu Gly Met His Ser Val Lys Tyr Val Asp Tyr His
785                 790                 795                 800

Phe Cys Gly Glu Ser Thr Thr Gly Ala Phe Pro Ser Leu Glu Ser Leu
                805                 810                 815

Lys Ile Gln Asp Met Met Cys Leu Met Ser Trp Tyr Pro Leu Ser Asp
                820                 825                 830

Asn Ser Leu Leu Gln Leu Arg Asp Leu Thr Ile Glu Asp Cys Pro Ser
                835                 840                 845

Leu Phe Ser Met Gln Ser Leu Lys His Met Ser Ser Leu Gln Glu Leu
    850                 855                 860

Val Ile Asn Cys Cys Pro Gly Leu Glu Thr Leu Pro Gln Leu Pro Gly
865                 870                 875                 880

Ser Val Gln Ser Leu Ile Ile Phe Gly Ser Asp Met Val Lys Gln Arg
                885                 890                 895

Cys Gln Ile Glu Glu Gly Pro Glu Trp Asn Met Ile Lys Thr Ile Pro
                900                 905                 910

Tyr Val Glu Ile Asp Tyr Glu Ser Met Phe Pro Gly Asp Ser Ser
        915                 920                 925

<210> SEQ ID NO 5
<211> LENGTH: 141
<212> TYPE: DNA
<213> ORGANISM: Artificial Sequence
<220> FEATURE:
<223> OTHER INFORMATION: Marker s3e4516s05
<220> FEATURE:
<221> NAME/KEY: misc_feature
<222> LOCATION: (71)..(71)
<223> OTHER INFORMATION: single nucleotide polymorphism: resistant: c
      (cytosine); sensitive: t (thymine)

<400> SEQUENCE: 5
agcacccaaa cctccgagar mycacccgat cactccaacy ccccatykcc ctcttcgccr      60
ccgccaacga nacaaccacc gcaagcccca caagaaagaa agcctcacaa ggcaatggac     120
gcggtrgaay taagrcgggt g                                               141

<210> SEQ ID NO 6
<211> LENGTH: 141
<212> TYPE: DNA
<213> ORGANISM: Artificial Sequence
<220> FEATURE:
<223> OTHER INFORMATION: Marker s3e5918s01
<220> FEATURE:
<221> NAME/KEY: misc_feature
<222> LOCATION: (71)..(71)
<223> OTHER INFORMATION: single nucleotide polymorphism: resistant: a
      (adenine); sensitive: g (guanine)
```

```
<400> SEQUENCE: 6
taagagatta wgtgtattar aatctccgac ctcatagtat cttaaagagc caaatctcca        60
taacggagtc natagcaaca aacctasata ttgtaggtaa tatctctcta agccagaagg       120
aacacttata gagtgtagag g                                                 141
```

RESISTANCE GENE TO RHIZOMANIA

CROSS-REFERENCE TO RELATED APPLICATIONS

This application is a U.S. National Phase of International Patent Application No. PCT/EP2017/070334, filed Aug. 10, 2017, which claims priority to European Patent Application No. 16183533.5, filed on Aug. 10, 2016, both of which applications are herein incorporated by reference in their entireties.

SEQUENCE LISTING

The instant application contains a Sequence Listing which has been filed electronically in ASCII format and is hereby incorporated by reference in its entirety. Said ASCII copy, created on Aug. 10, 2017, is named U.S. Ser. No. 16/323,884.txt and is 24,686 bytes in size.

FIELD OF THE INVENTION

The present invention relates to a nucleic acid molecule, which encodes a polypeptide that is capable of imparting a resistance to a pathogen, in particular beet necrotic yellow vein virus (BNYVV), in a plant, in particular of the genus *Beta*, in which the polypeptide is expressed, and also to the polypeptide encoded by the nucleic acid molecule according to the invention. The invention further relates to a transgenic plant, plant cell, plant organ, plant tissue, plant part or a seed of a plant which comprises the nucleic acid molecule or parts thereof, as well as a BNYVV-resistant plant or parts thereof, in which the resistance is produced by introducing one or more mutations into the endogenous nucleic acid molecule. The invention also relates to a method for producing such a transgenic plant or plant cell and the BNYVV-resistant non-transgenic plant. The invention further relates to marker-based methods for identifying and selecting a BNYVV-resistant plant and to a method for controlling infestation with the pathogen BNYVV.

BACKGROUND OF THE INVENTION

Worldwide, rhizomania is the economically most important sugar beet disease and can cause yield losses of 50% and more. The disease, which in German is also referred to literally translated as "root beardedness," is caused by beet necrotic yellow vein virus (BNYVV) and transmitted by the soil-borne protozoan *Polymyxa betae*. A BNYVV infection manifests itself in an increased proliferation of the thin roots and secondary roots and in the formation of a greatly reduced root body with reduced sugar content. Infected plants exhibit reduced water absorption and are thus more sensitive to drought stress. The spread of the infection to the whole plant results in yellowing of the leaf veins, necrotic lesions and yellow spots on the leaves. Because curative control of the disease is not possible, as is the case for other viral diseases, damage can be prevented only via the cultivation of resistant types. The development of genotypes having a genetic resistance to rhizomania is thus vital for the cultivation of sugar beets.

The first breeding programs for rhizomania resistance started in 1981 in Italy, when it was discovered that a satisfactory degree of genetic variability for rhizomania resistance exists in commercial germplasms. Plants and genotypes that exhibited lesser disease symptoms and almost normal root weight and sugar content were selected. A multigenic source of resistance named "Alba type" was successfully identified from crosses with *Beta vulgaris* L subsp. *maritima* (L).

A further type of resistance, which exhibited improved protection against rhizomania, was developed in 1982. This emerged two years later in the variety Rizor and was classified as a monogenic, dominant resistance. A further monogenic, dominant resistance was discovered in 1983 during variety tests in California at the breeding company Holly Sugar Company and introduced just three years later, also in Europe (Lewellen et al. 1987). This resistance, known as RZ-1 (also referred to as "Holly"), developed into the most used source and quickly took the place of Rizor. A few years later, a new source of rhizomania resistance was discovered in *Beta maritima* accession WB42 from Denmark. It showed a mapping position on chromosome III different to that of RZ-1 and also provided an increased level of resistance in comparison to RZ-1. This new major gene was referred to as RZ-2. Since then, RZ-3 from the *Beta maritima* accession WB41, which is probably an allelic variant of RZ-2, has become known as well.

To date, RZ-3 is the only rhizomania resistance gene for which the functional background, i.e. the genetic structure, has been clarified (see the German patent application DE 10 2013 010 026 A2). As a result, it has been possible to improve the use of the gene for breeding significantly. There is therefore the longstanding desire to better describe both the already known and the new source of resistances genetically, in order to thereby drive the development of molecular markers. Elite sugar beet lines could consequently be further optimized by eliminating linkage drag, and new sources of resistance could be identified, as well.

For sustainable breeding against rhizomania, which is intended to counteract the risk of resistance-breaking BNYVV isolates, it is necessary to constantly identify new resistance genes and integrate them into the gene pools of crop plants such as sugar beet. This object is achieved according to the invention by the embodiments characterized in the claims and in the description.

SUMMARY OF THE INVENTION

The present invention relates to a nucleic acid molecule that is capable of imparting a resistance to a pathogen, in particular to beet necrotic yellow vein virus (BNYVV), in a plant, in particular of the genus *Beta*, in which a polypeptide encoded by the nucleic acid molecule is expressed. The invention further relates to a plant, in particular a transgenic plant, plant cell, plant organ, plant tissue, plant part or a seed of a plant, which comprises the nucleic acid molecule or parts thereof, as well as a BNYVV-resistant plant or parts thereof, in which the resistance is imparted by introducing one or more mutations into the endogenous nucleic acid molecule. The invention also relates to a method for producing such a transgenic plant or plant cell and the BNYVV-resistant non-transgenic plant. The invention further includes marker-based methods for identifying and selecting a BNYVV-resistant plant and a method for controlling infestation with the pathogen BNYVV.

The present invention therefore relates to the embodiments, which are listed in the following points [1] to [22] and illustrated in the examples and FIGURES.

[1] Nucleic acid molecule, which encodes a polypeptide that is capable of imparting a resistance to a pathogen in a plant in which the polypeptide is expressed, characterized in that the nucleic acid molecule comprises a nucleotide sequence selected from (a) a nucleotide sequence that encodes a polypeptide having an amino acid sequence as per SEQ ID NO: 2 or a polypeptide having an amino acid sequence that is at least 70% identical to SEQ ID NO: 2, in which at least one amino acid substitution is present as a result of one or more mutations of the nucleotide sequence, preferably lysine (K) at position 307 and/or glutamine (Q) at 437;

(b) a nucleotide sequence that comprises the sequence as per SEQ ID NO: 1 or that hybridizes with the complementary sequence to SEQ ID NO: 1 under stringent conditions, in which a nucleotide substitution is present as a result of one or more mutations, which leads to an amino acid substitution, preferably at positions 919-921 and/or 1309-1311;

(c) a nucleotide sequence that encodes a polypeptide which, by substitution, deletion and/or addition from one or more amino acids of the amino acid sequence encoded by the nucleotide sequence according to (a) or (b), is derived from a polypeptide encoded by the nucleotide sequence according to (a) or (b), or (d) a nucleotide sequence that encodes at least one leucine-rich domain (LRR) corresponding to (i) the amino acid positions 558 to 594 of SEQ ID NO: 4, preferably the amino acid positions 542 to 594 of SEQ ID NO: 4, (ii) the amino acid positions 604 to 634 of SEQ ID NO: 4, preferably the amino acid positions 582 to 634 of SEQ ID NO: 4, (iii) the amino acid positions 760 to 790 of SEQ ID NO: 4 or (iv) the amino acid positions 838 to 869 of SEQ ID NO: 4, and/or at least one AAA ATPase domain corresponding to (I) the amino acid positions 177 to 289 of SEQ ID NO: 4 or (II) the amino acid positions 156 to 263 of SEQ ID NO: 4, preferably wherein the pathogen is beet necrotic yellow vein virus (BNYVV) and the plant is a plant of the genus *Beta*, preferably sugar beet (*Beta vulgaris* L.).

[2] Nucleic acid molecule according to [1], characterized in that the encoded polypeptide alternatively or additionally comprises (i), at that position which in the reference amino acid sequence SEQ ID NO: 2 corresponds to position 566, an amino acid that differs from arginine (R), and/or (ii), at that position which in the reference amino acid sequence SEQ ID NO: 2 corresponds to position 731, an amino acid that differs from glutamine (Q), and/or (iii), at that position which in the reference amino acid sequence SEQ ID NO: 2 corresponds to position 831, an amino acid that differs from proline (P).

[3] Nucleic acid molecule according to [1] or [2], characterized in that the encoded polypeptide (i) comprises a glutamine (Q) at that position which in the reference amino acid sequence SEQ ID NO: 2 corresponds to position 307, and/or (ii) comprises an arginine (R) at that position which in the reference amino acid sequence SEQ ID NO: 2 corresponds to position 437, and/or (iii) comprises a histidine (H) at that position which in the reference amino acid sequence SEQ ID NO: 2 corresponds to position 566, and/or (iv) comprises a lysine (K) at that position which in the reference amino acid sequence SEQ ID NO: 2 corresponds to position 731, and/or (v) comprises a serine (S) at that position which in the reference amino acid sequence SEQ ID NO: 2 corresponds to position 831.

[4] Nucleic acid molecule according to [3], characterized in that, at those locations which correspond to the locations in the reference nucleotide sequence SEQ ID NO: 1, the nucleic acid molecule comprises one or more of the following nucleotide substitutions:

(a) C instead of A at position 919;

(b) G instead of A at position 1310;

(c) A instead of G at position 1697;

(d) A instead of C at position 2191; and/or (e) T instead of C at position 2491.

[5] Nucleic acid molecule according to [1] to [4], characterized in that the nucleic acid molecule encodes a polypeptide having an amino acid sequence as per SEQ ID NO: 4 and/or comprises the encoding DNA sequence as per SEQ ID NO: 3.

[6] Vector, which comprises the nucleic acid molecule according to any one of [1] to [5].

[7] Host cell, which comprises the nucleic acid molecule according to any one of [1] to [5] or the vector according to [6].

[8] Polypeptide, which is encoded by the nucleic acid molecule according to any one of [1] to [5], or an antibody directed against the polypeptide.

[9] Transgenic plant cell, preferably from a plant of the genus *Beta*, which comprises the nucleic acid molecule according to any one of [1] to [5] as a transgene, optionally under the control of a heterologous promoter, or the vector according to [6].

[10] Transgenic plant, preferably of the genus *Beta*, or a part thereof, which comprises a plant cell according to [9].

[11] BNYVV-resistant plant of the genus *Beta* or a part thereof, in which the nucleic acid molecule according to any one of [1] to [5] is endogenously present, or in which the one or more mutations defined in any one of [1] to [4] have been introduced into an endogenous nucleic acid molecule having a nucleotide sequence that comprises the sequence as per SEQ ID NO: 1 or that hybridizes with the complementary sequence to SEQ ID NO: 1 under stringent conditions, wherein the plant or a part thereof does not belong to the subspecies *Beta vulgaris* subsp. *maritima*.

[12] Plant according to [10] or [11], characterized in that the plant is a hybrid plant or a double-haploid plant.

[13] Plant according to any one of [10] to [12], characterized in that the nucleic acid molecule or the one of the plurality of mutations is heterozygous or homozygous.

[14] Plant according to any one of [10] to [13], additionally transgenically or endogenously comprising a second nucleic acid molecule in the genome, preferably at another or further position in the genome, which encodes a polypeptide that is capable of imparting a resistance to BNYVV in said plant, in which the polypeptide is expressed as a result of the transcription of the second nucleic acid molecule.

[15] Seed of the plant according to any one of [10] to [14], wherein the seed transgenically or endogenously comprises one or more of the aforementioned nucleic acid molecules or vectors.

[16] Method for producing a transgenic plant cell and/or a transgenic plant, characterized in that the method comprises a step of introducing the nucleic acid molecule according to any one of [1] to [5] or the vector according to [6] into the plant cell, and optionally regenerating the transgenic plant from the transgenic plant cell.

[17] Method for producing a BNYVV-resistant plant, comprising the following steps:
(a) Mutagenizing of plant cells and subsequent regeneration of plants from the mutagenized plant cells or mutagenizing of plants, and optionally
(b) Identifying a plant from (a) which, in an endogenous nucleic acid molecule, comprises the one or more mutations defined in any one of [1] to [5].
[18] Method for identifying a plant of the genus *Beta* that is resistant to the pathogen BNYVV, characterized in that the method comprises the following step
(i) detecting the presence and/or expression of the nucleic acid molecule according to any one of [1] to [5] in the plant or in a sample thereof; and/or
(ii) detecting at least one marker locus in the nucleotide sequence of the nucleic acid molecule according to any one of [1] to [5] or the immediate vicinity, preferably on chromosome III; and/or
(iii) detecting at least two marker loci on chromosome III in the plant, wherein at least one marker locus is located on or within the chromosomal interval from s3e4516s05 (SEQ ID NO: 5) to the nucleic acid molecule according to any one of [1] to [5] and at least one marker locus is located on or within the chromosomal interval from the nucleic acid molecule according to any one of [1] to [5] to s3e5918s01 (SEQ ID NO: 6); as well as optionally
(iv) selecting the BNYVV-resistant plant.
[19] Method according to [18], characterized in that the at least one marker locus comprises the one or more mutations defined in any one of [1] to [5].
[20] Plant or a part thereof that has been identified and optionally selected using a method according to [18] or [19].
[21] Population of plants including plants according to any one of [11] to [13] or [20].
[22] Method for controlling infestation with the pathogen beet necrotic yellow vein virus (BNYVV) in the agricultural or horticultural cultivation of plants of the genus *Beta*, comprising I) the identification and selection of plants of the genus *Beta* with the aid of a method according to [18] or [19] and II) the cultivation of the plants from I) or the progeny thereof.
[23] Use of a plant cell according to [9], plant according to any one of [10] to [14] or [20] or organs, plant parts, tissue or cells thereof, a seed according to [15] or a plant obtainable by the method according to [16] or [17] or selected according to [18] or [19], or organs, plant parts, tissue, cells, progeny or seeds thereof, in the production of foodstuffs, materials, pharmaceuticals or precursors thereof, diagnostic agents, cosmetics, fine chemicals, sugar, syrup, bioethanol or biogas.

Some of the terms used in this application are first explained in more detail in the following:

The term "approximately" in the context of specifying a length of a nucleotide sequence means a deviation by +/−10,000 base pairs, +/−5,000 base pairs or +/−1,000 base pairs, preferably by +/−200 base pairs or +/−100 base pairs and particularly preferably +/−50 base pairs.

A "plant of the genus *Beta*" belongs to the foxtail family (Amaranthaceae). These plants include plants of the species *Beta macrocarpa*, *Beta vulgaris*, *Beta lomatogona*, *Beta macrorhiza*, *Beta coroffiflora*, *Beta trigyna* and *Beta nana*. A plant of the species *Beta vulgaris* is, in particular, a plant of the subspecies *Beta vulgaris* subsp. *vulgaris*. These include, for example, *Beta vulgaris* subsp. *vulgaris* var. *altissima* (sugar beet in the narrower sense), *Beta vulgaris* ssp. *vulgaris* var. *vulgaris* (chard), *Beta vulgaris* ssp. *vulgaris* var. *conditiva* (red beet/beetroot), *Beta vulgaris* ssp. *vulgaris* var. *crassa/alba* (fodder beet).

The term "hybridize" or "hybridization" is understood to mean a process in which a single-stranded nucleic acid molecule attaches to a nucleic acid strand that is complementary to the greatest possible extent, i.e. forms base pairs with said strand. Standard methods for hybridization are described, for example, in Sambrook et al., *Molecular Cloning: A Laboratory Manual*, 3$^{rd}$ Ed. Cold Spring Harbor Laboratory Press, Cold Spring Harbor, N.Y., 2001. It is preferably understood to mean that at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule form a base pairing with the nucleic acid strand that is complementary to the greatest possible extent. The possibility of such an attachment is a function of the stringency of the hybridization conditions. The term "stringency" relates to the hybridization conditions. High stringency exists when base pairing is hindered, and low stringency exists when base pairing is facilitated. The stringency of the hybridization conditions is, for example, a function of the salt concentration or ionic strength and the temperature. The stringency can generally be increased with an increase of the temperature and/or a lowering of the salt content. "Stringent hybridization conditions" are conditions in which hybridization predominantly occurs only between homologous nucleic acid molecules. The term "hybridization conditions" does not relate only to the conditions prevailing during the actual attachment of the nucleic acids, but also to the conditions prevailing during the subsequent washing steps. Stringent hybridization conditions are, for example, conditions under which predominantly only those nucleic acid molecules hybridize that have at least 70%, preferably at least 75%, at least 80%, at least 85%, at least 90% or at least 95% sequence identity. Stringent hybridization conditions are, for example: hybridization in 4×SSC at 65° C. and subsequent repeated washing in 0.1×SSC at 65° C. for approximately 1 hour in total. The term "stringent hybridization conditions" used here may also mean: hybridization at 68° C. in 0.25 M sodium phosphate, pH 7.2, 7% SDS, 1 mM EDTA and 1% BSA for 16 hours and subsequent washing twice with 2×SSC and 0.1% SDS at 68° C. Hybridization preferably takes place under stringent conditions.

In the context of a nucleic acid in the form of a double-stranded DNA, "complementary" nucleotide sequence means that the second DNA strand, which is complementary to the first DNA strand, comprises nucleotides that correspond to the bases of the first strand in accordance with the base pairing rules.

An "isolated nucleic acid molecule" is a nucleic acid molecule that has been separated out of its natural or original environment. The term also includes a synthetically produced nucleic acid molecule. An "isolated polypeptide" is a polypeptide that has been separated out of its natural or original environment. The term also includes a synthetically produced polypeptide.

A "molecular marker" is a nucleic acid that is polymorphous in a plant population and is used as a reference or orientation point. A marker for detecting a recombination event should be suitable for monitoring differences or polymorphisms within a plant population. Such a marker is thus able to detect and differentiate different allelic states (alleles). The term "molecular marker" also refers to nucleotide sequences that are complementary or at least complementary to the greatest possible extent or homologous to genomic sequences, for example nucleic acids used as probes or primers.

For markers, these differences are found on the DNA level and are, for example, polynucleotide sequence differences such as SSRs (simple sequence repeats), RFLPs (restriction fragment length polymorphisms), FLPs (fragment length polymorphisms) or SNPs (single nucleotide polymorphisms). The markers can be derived from genomic or expressed nucleic acids such as spliced RNA, cDNA or ESTs, and can also refer to nucleic acids that are used as probes or primer pairs and are suitable, as such, to amplify a sequence fragment using PCR-based methods. Markers that describe genetic polymorphisms (between parts of a population) can be detected using well-established methods from the state of the art (*An Introduction to Genetic Analysis*, 7th Edition, Griffiths, Miller, Suzuki et al., 2000). These include, for example, DNA sequencing, PCR-based sequence-specific amplification, detection of RFLPs, detection of polynucleotide polymorphisms by means of allele-specific hybridization (ASH), detection of amplified variable sequences of the plant genome, detection of a 3SR (self-sustained sequence replication), detection of SSRs, SNPs, RFLPs or AFLPs (amplified fragment length polymorphisms). Further known are also methods for detecting ESTs (expressed sequence tags) and SSR markers derived from EST sequences and RAPD (randomly amplified polymorphic DNA). Depending on the context, the term "marker" in the description can also mean a specific chromosome position in the genome of a species, in which a specific marker (e.g. SNP) can be found.

A "promoter" is an untranslated regulatory DNA sequence, typically upstream of an encoding region, which contains the binding site for the RNA polymerase and initiates the transcription of the DNA. A promoter also contains other elements that function as the regulator gene for gene expression (e.g. cis-regulatory elements). A "core or minimal promoter" is a promoter that comprises at least the basic elements needed to initiate transcription (e.g. TATA box and/or initiator).

A "pathogen" is an organism that, in interaction with a plant, leads to disease symptoms on one or more organs of the plant. These pathogens include, for example, animal, fungal, bacterial or viral organisms or oomycetes.

A "pathogen infection" is the earliest point in time at which a pathogen interacts with a plant host tissue. The viral pathogen BNYVV, for example, is transmitted by the protozoan *Polymyxa betae*. *Polymyxa* generates spores that can survive in the ground for many decades. The virus also survives in these spores. When these dormant spores germinate to form mobile zoospores, the virus can pass into cells of the plant host tissue via said spores and interact there with the host (Esser (2000) *Kryptogamen 1: Cyanobakterien Algen Pilze Flechten Praktikum and Lehrbuch* [Cryptogams 1: Cyanobacteria, Algae, Fungi, and Lichens Practical Guide and Textbook]. Springer Publishing House, Berlin, Heidelberg, 3$^{rd}$ Edition).

Plant "organs" are, for example, leaves, shoot axis, trunk, roots, hypocotyl, vegetative buds, meristems, embryos, anthers, ovules, seed grains or fruits. "Plant parts" include, but are not restricted to the shoot axis or the stem, leaves, flowers, inflorescences, roots, fruits and seeds as well as pollen. The term "plants parts" further means a combination of multiple organs, e.g. a flower or a seed, or part of an organ, e.g. a cross section through the shoot axis. Plant "tissue" is, for example, callus tissue, storage tissue, meristematic tissue, leaf tissue, shoot tissue, root tissue, plant tumor tissue or reproductive tissue as well as formative tissue, basal tissue (the so-called parenchyma), vascular tissue, strengthening tissue and the covering tissue (the so-called epidermis). The type of tissue is, however, not restricted by this listing. Plant "cells" are, for example, isolated cells having a cell wall or aggregates thereof or protoplasts.

In the context of the present invention, the term "regulatory sequence" relates to a nucleotide sequence that affects specificity and/or expression strength, for example in that the regulatory sequence imparts a particular tissue specificity. Such a regulatory sequence can be located upstream of the transcription initiation point of a minimal promoter, or also downstream thereof, for example in a transcribed but untranslated leader sequence or within an intron.

The term "resistance" is to be understood broadly and covers the scope of protection from a delay to a complete inhibition of the development of the disease. One example of a pathogen of significance is beet necrotic yellow vein virus (BNYVV). A resistant plant cell according to the invention or resistant plant according to the invention preferably achieves a resistance to BNYVV. A resistance to a pathogen is to be equated with a resistance to the disease caused by said pathogen. A resistance to BNYVV, for example, is also a resistance to rhizomania.

"Transgenic plant" refers to a plant into the genome of which at least one polynucleotide is integrated. This can be a heterologous polynucleotide. The polynucleotide is preferably integrated in a stable manner, which means that the integrated polynucleotide remains stable in the plant, is expressed, and can also be passed on in a stable manner to the progeny. The stable introduction of a polynucleotide into the genome of a plant also includes integration into the genome of a plant of the preceding parental generation, whereby the polynucleotide can be passed on in a stable manner. The term "heterologous" means that the introduced polynucleotide originates from a cell or an organism having a different genetic background of the same species or a different species, for example, or is homologous to the prokaryotic or eukaryotic host cell, but is then located in a different genetic environment and thus differs from a possibly naturally present corresponding polynucleotide. A heterologous polynucleotide can be present in addition to a corresponding endogenous gene.

Forms and embodiments of the present invention are described in an exemplary manner with reference to the accompanying sequences and FIGURES.

BRIEF DESCRIPTION OF THE FIGURES

FIG. 1: (A) Genomic DNA sequence of the rhizomania (WB) sensitive allele wb-s of the resistance gene wb (SEQ ID NO: 1) from an SS-genotype, which has been identified as NBS-LRR (NB-ARC domain gene) by means of fine mapping. The analysis of the progeny of the 4 most closely recombinant plants (2 direct recombinants to the left and two direct recombinants to the right around the gene) narrowed the location of the NBS-LRR gene down to one gene. The shown sequence comprises the encoding region of the predicted protein sequence (B, SEQ ID NO: 2) of the resistance protein WB-s. (C) Genomic DNA sequence of a WB-resistant allele wb-R of the resistance gene wb (SEQ ID NO: 3) comprising the encoding region of the predicted protein sequence. Diagnostic polymorphisms that lead to amino acid substitutions are underlined and highlighted in bold. (D) Amino acid sequence of a protein encoded by the genomic DNA sequence of a WB-resistant allele wb-R of the resistance gene wb (SEQ ID NO: 4). Diagnostic polymorphisms are underlined and highlighted in bold. Experiments within the framework of the present invention, including sequence analyses of the WB-resistant genotypes versus the prevailing sensitive genotype and the amino acid sequence listed in the genome database, showed that, in the genomic DNA sequence of the WB-resistant wb-R alleles, the correlating NBS-LRR gene with the reading frame shown in SEQ ID NO: 3 exhibits one or more amino acid substitutions, so that the observed resistance can be attributed to mutations in this gene. Based on the analysis to date of the recombinants, in particular one of the two amino acid substitutions K307Q and/or Q437R can be regarded as causative for resistance.

DETAILED DESCRIPTION OF THE INVENTION

The present invention relates to a nucleic acid molecule that is capable of imparting a resistance to a pathogen, in particular to beet necrotic yellow vein virus (BNYVV), in a plant, in particular of the genus *Beta*, in which a polypeptide encoded by the nucleic acid molecule is expressed. The present invention is based on genetic fine mapping, identification, isolation and characterization of a gene originating from the donor *Beta vulgaris* subsp. *Maritima*, the presence of which in a plant, in particular in a sugar beet, correlates to or is causative for the resistance of the plant in question to rhizomania (WB), and the nucleotide and encoded amino acid sequence of which is characterized by at least one nucleotide or amino acid substitution with respect to the nucleotide or amino acid sequence of the NBS-LRR gene identified according to the invention shown in FIGS. 1A and B, wherein the nucleotide or amino acid substitutions preferably account for no more than 50%, preferably no more than 60%, more preferably no more than 70%, even more preferably no more than 80%, yet more preferably no more than 90% and particularly preferably no more than 95% relative to the nucleotide and amino acid sequence as a whole shown in FIGS. 1A and B. Particularly preferred embodiments of nucleotide and amino acid sequences of the nucleic acid molecule according to the invention are shown in FIGS. 1C and D and described in the examples and the legend of the FIGURE.

The nucleic acid molecule can be an isolated nucleic acid molecule. It is preferably DNA, and particularly preferably cDNA or encoding DNA. The polypeptide encoded by the nucleic acid molecule according to the invention preferably imparts a resistance to the viral pathogen beet necrotic yellow vein virus (BNYVV), which causes the plant disease rhizomania and is transmitted by the soil-borne protozoan *Polymyxa betae*. The polypeptide encoded by the nucleic acid molecule according to the invention further imparts a resistance to said pathogen in particular in a plant of the genus *Beta*. The plant is preferably a plant of the *Beta vulgaris* species, particularly preferably a plant of the subspecies *Beta vulgaris* subsp. *vulgaris*; these include, for example, the cultivars sugar beet, red beet, fodder beet, leaf chard and stem chard.

In one embodiment of the present invention, the nucleic acid molecule according to the invention comprises a nucleotide sequence that encodes a polypeptide having an amino acid sequence as per SEQ ID NO: 2, wherein the nucleic acid molecule has one or more mutations as a result of which, at that position which in the reference amino acid sequence SEQ ID NO: 2 corresponds to position 307, the polypeptide encoded by the nucleic acid molecule comprises an amino acid that differs from lysine (K) and/or, at that position which in the reference amino acid sequence SEQ ID NO: 2 corresponds to position 437, said polypeptide comprises an amino acid that differs from glutamine (Q). One of the two or both of the mentioned mutations in the amino acid sequence have been identified as the suspected causative factor for the resistance to rhizomania.

As explained in the examples and in the legend of the FIGURE, the gene identified according to the invention is a resistance gene/protein of the NBS-LRR type, which is characterized by certain structural motifs. The general structure of such resistance proteins in plants has already been studied extensively (Martin et al., *Annual Review Plant Biology* 54 (2003), 23-61). However, the principle of the structural form, in particular of the so-called LRR domain, which is considered to be the potential recognition domain for mostly unknown pathogenic effectors, is not predictable, and the functional background of the resistance genes, i.e. the genetic structure, is generally largely unknown. Consequently, the identification of a BNYVV resistance-imparting gene or protein solely on the basis of the known structural motifs is not possible. The sequence regions around these resistance genes are also often repetitive, which makes the development of diagnostic markers and the assembly of sequences particularly difficult.

The identified resistance protein belongs to the type NBS-LRR and has at least one leucine-rich domain (LRR) encoded corresponding to the amino acid positions 558 to 594 of SEQ ID NO: 4, preferably the amino acid positions 542 to 594 of SEQ ID NO: 4, the amino acid positions 604 to 634 of SEQ ID NO: 4, preferably the amino acid positions 582 to 634 of SEQ ID NO: 4, the amino acid positions 760 to 790 of SEQ ID NO: 4 or the amino acid positions 838 to 869 of SEQ ID NO: 4, and/or at least one AAA ATPase domain corresponding to the amino acid positions 177 to 289 of SEQ ID NO: 4 or the amino acid positions 156 to 263 of SEQ ID NO: 4. The identified ATPase domain is most likely the NB-ARC domain, which has a central nucleotide-binding function. Without being bound to one specific theory, said functional ATPase domain presumably regulates the activity of the resistance protein.

In a further embodiment, the nucleic acid molecule according to the invention comprises the nucleotide sequence of SEQ ID NO: 1, wherein one or more nucleotides are substituted at positions 919-921 and/or 1309-1311, which results in an amino acid substitution.

These amino acid substitutions or nucleotide substitutions can be carried out using conventional methods known in the state of the art, for example using site-directed mutagenesis, PCR-mediated mutagenesis, transposon mutagenesis, TILLING, genome engineering, for example using meganucleases, zinc-finger nucleases, TALENs and CRISPR/Cas, etc. Further substitutions, deletions, insertions, additions and/or any other change can furthermore additionally be introduced into the nucleotide sequence, either alone or in combinations. These change the nucleotide sequence, but fulfill the same function as the starting sequence, in this case the nucleotide sequence according to the invention, which encodes a polypeptide with the amino acid sequence according to the invention that imparts resistance to rhizomania. Therefore, in a further embodiment, the invention includes a nucleotide sequence that encodes a polypeptide which represents a derivative of the polypeptide that is encoded by the nucleotide sequence according to the invention or that comprises the amino acid sequence according to the invention. A derivative of the polypeptide represents a derived amino acid sequence having at least one substitution, deletion, insertion or addition of one or more amino acids, wherein the functionality of the encoded polypeptide/protein is preserved.

The substitution of an amino acid by another amino acid having the same or equivalent or similar chemical-physical properties is referred to as a "conservative substitution" or a "semi-conservative substitution." Examples of physical-chemical properties of an amino acid are the hydrophobicity or the charge. The person skilled in the art knows which amino acid substitution represents a conservative or semi-conservative substitution. The common general knowledge also allows the person skilled in the art to recognize, identify and detect which amino acid deletions and additions are harmless to the functionality of the resistance protein and at which positions these are possible. The person skilled in the art is aware that, in the case of the present NBS-LRR proteins for modifications of the amino acid sequence (substitutions, deletions, insertion or additions of one or more amino acids), in particular the functionality of the above-defined conserved domains must be preserved, and that therefore the abovementioned modifications are possible only to a limited extent in these domains.

The invention therefore relates to a functional fragment of the nucleotide sequence according to the invention. The term "fragment" includes genes having a nucleotide sequence that is sufficiently similar to the abovementioned nucleotide sequence. The term "sufficiently similar" means a first nucleotide sequence or amino acid sequence that has a sufficient or minimal number of identical or equivalent nucleotides or amino acid residues relative to a second nucleotide or a second amino acid sequence.

As for the amino acid sequence, even after modification with an abovementioned method, said amino acid sequence has a common structural domain and/or possesses a common functional activity. Nucleotide sequences or amino acid sequences, the identity of which is at least 70%, at least 75%, at least 80%, at least 85%, at least 90%, at least 91%, at least 92%, at least 93%, at least 94%, at least 95%, at least 96%, at least 97%, at least 98%, at least 99%, or 100% similar to the nucleotide sequence or amino acid sequence according to the invention are defined here as being sufficiently similar. For the functional fragments, a sufficient similarity is preferably substantiated when the nucleotide sequence or amino acid sequence generally exhibits the same property as the previously mentioned nucleotide or amino acid sequences of the present invention. Such nucleotide sequences, which encode for a derivative or for a derived amino acid sequence, can preferably be produced either directly or indirectly (for example via amplification or replication steps) from a starting nucleotide sequence, which corresponds to the nucleotide sequence according to the invention at least partially or over the entire length.

The present invention accordingly comprises a nucleotide sequence that is capable of hybridizing under stringent conditions to a nucleotide sequence, which is complementary to a nucleotide sequence according to the invention or to the nucleotide sequence that encodes the amino acid sequence according to the invention.

In a further embodiment of the present invention, the nucleic acid molecule according to the invention comprises a nucleotide sequence, which encodes at least one leucine-rich domain (LRR) corresponding to the amino acid positions 558 to 594 of SEQ ID NO: 4, preferably the amino acid positions 542 to 594 of SEQ ID NO: 4, the amino acid positions 604 to 634 of SEQ ID NO: 4, preferably the amino acid positions 582 to 634 of SEQ ID NO: 4, the amino acid positions 760 to 790 of SEQ ID NO: 4 or the amino acid positions 838 to 869 of SEQ ID NO: 4, and/or at least one AAA ATPase domain corresponding to the amino acid positions 177 to 289 of SEQ ID NO: 4 or the amino acid positions 156 to 263 of SEQ ID NO: 4. These domains are particularly preferably sequentially present in the polypeptide from the N- to the C-terminus in the sequence AAA ATPase-LRR, wherein one or more further amino acids can respectively be present between domains.

In a further embodiment, the nucleic acid molecule according to the invention comprises a nucleotide sequence that encodes a polypeptide having an amino acid sequence as per SEQ ID NO: 2, wherein the nucleic acid molecule has one or more mutations as a result of which, at that position which in the reference amino acid sequence SEQ ID NO: 2 corresponds to position 307, the polypeptide encoded by the nucleic acid molecule comprises an amino acid that differs from lysine (K) and/or, at that position which in the reference amino acid sequence SEQ ID NO: 2 corresponds to position 437, an amino acid that differs from glutamine (Q) and, at that position which in the reference amino acid sequence SEQ ID NO: 2 corresponds to position 566, an amino acid that differs from arginine (R), and/or (ii), at that position which in the reference amino acid sequence SEQ ID NO: 2 corresponds to position 731, an amino acid that differs from glutamine (Q), and/or (iii), at that position which in the reference amino acid sequence SEQ ID NO: 2 corresponds to position 831, an amino acid that differs from proline (P). As mentioned above, the first two substitutions have been identified as being responsible for the resistance. Although the role of the last three substitutions in imparting the resistance is still unclear, they are diagnostic and can thus advantageously be used in detection and/or selection methods.

In a further embodiment, the nucleic acid molecule according to the invention comprises a nucleotide sequence that encodes a polypeptide having an amino acid sequence as per SEQ ID NO: 2, wherein the encoded polypeptide comprises a glutamine (Q) at that position which in the reference amino acid sequence SEQ ID NO: 2 corresponds to position 307, and/or comprises an arginine (R) at that position which in the reference amino acid sequence SEQ ID NO: 2 corresponds to position 437, and/or comprises a histidine (H) at that position which in the reference amino acid sequence SEQ ID NO: 2 corresponds to position 566, and/or comprises a lysine (K) at that position which in the reference amino acid sequence SEQ ID NO: 2 corresponds to position 731, and/or comprises a serine (S) at that position which in the reference amino acid sequence SEQ ID NO: 2 corresponds to position 831. Said amino acid substitutions preferably occur by substitution of one or more nucleotides in the nucleic acid molecule of SEQ ID NO: 1, wherein one nucleotide is preferably substituted with another. The nucleic acid molecule according to the invention is consequently characterized in that, at those locations which correspond to the locations in the reference nucleotide sequence SEQ ID NO: 1, the nucleic acid molecule comprises one or more of the following nucleotide substitutions: C instead of A at position 919; G instead of A at position 1310; A instead of G at position 1697; A instead of C at position 2191; and/or T instead of C at position 2491. In a preferred embodiment, the nucleic acid molecule according to the invention is characterized in that it encodes a polypeptide having an amino acid sequence as per SEQ ID NO: 4 and/or comprises the encoding DNA sequence as per SEQ ID NO: 3; see also FIG. 1 and the accompanying FIGURE legend as well as the examples.

The invention further relates to a recombinant DNA molecule comprising the sequences of the nucleic acid molecule according to the invention. The recombinant DNA molecule preferably further comprises a regulatory sequence or is associated with/operatively linked to said sequence, preferably with a promoter sequence and/or other sequences of transcription or translation control elements, wherein the regulatory sequence which controls the expression of a gene comprising the nucleic acid molecule according to the invention is characterized in that the regulatory sequence is able to impart or modulate the expression of a heterologous DNA sequence as a result of a pathogen infection. The heterologous DNA sequence is preferably a nucleotide sequence that encodes for a component of the plant pathogen defense (e.g.: resistance gene (R-gene) or genes that encode for enzymes involved in signal transfer, such as kinases or phosphatases and for G-protein) or that encodes for a pathogenic effector (so-called avirulence genes (Avr)).

The present invention further relates to a polypeptide, which can be encoded by the nucleic acid molecule according to the invention, and to a functional and/or immunologically active fragment thereof as well as to an antibody that binds specifically to said polypeptide or to its fragment.

The polypeptide particularly preferably comprises an amino acid sequence as per SEQ ID NO: 4. The recombinant production of proteins, polypeptides and fragments is familiar to the person skilled in the art and is described, for example, in Sambrook et al., *Molecular Cloning: A Laboratory Manual* 3$^{rd}$ Ed. Cold Spring Harbor Laboratory Press, Cold Spring Harbor, N.Y., 2001 or Wingfield, P. T. 2008, *Production of Recombinant Proteins, Current Protocols in Protein Science,* 52:5.0: 5.0.1-5.0.4. Polyclonal or monoclonal antibodies to the protein of the present invention can be produced by the person skilled in the art using known methods, as described in E. Harlow et al., Editors, *Antibodies: A Laboratory Manual* (1988). The production of monoclonal antibodies and of Fab and F(ab')2 fragments, which are also useful for protein detection methods, can be carried out using a variety of conventional methods as described in Goding, *Monoclonal Antibodies: Principles and Practice*, p. 98-118, New York: Academic Press (1983). The antibody can then be used to screen expression cDNA libraries to identify identical, homologous or heterologous genes by means of immunological screening (Sambrook et al., *Molecular Cloning: A Laboratory Manual*, Cold Spring Harbor Laboratory Press, Cold Spring Harbor, N.Y., 1989 or Ausubel et al., 1994, *Current Protocols in Molecular Biology*, John Wiley & Sons). The present invention relates in particular to antibodies that selectively detect a polypeptide encoded by the wb-R allele according to the invention and for the most part not the polypeptide encoded by the sensitive wb-S allele, i.e. by at least a factor of 2, preferably a factor of 5, and more preferably by a factor of 10 or more less than the polypeptide encoded by the wb-R allele according to the invention.

The invention further relates to vectors, which comprise the nucleic acid molecule or the recombinant DNA molecule according to the invention. The vector can be a plasmid, a cosmid, a phage or an expression vector, a transformation vector, shuttle vector or cloning vector; it can be double or single-stranded, linear or circular, or can transform a prokaryotic or eukaryotic host either by integration into its genome or extrachromosomally. The nucleic acid molecule or DNA molecule according to the invention is preferably operatively linked in an expression vector to one or more regulatory sequences, which allow transcription and optionally expression in a prokaryotic or eukaryotic host cell; see, for example, Sambrook et al., *Molecular Cloning: A Laboratory Manual* 3$^{rd}$ Ed. Cold Spring Harbor Laboratory Press, Cold Spring Harbor, N.Y., 2001. Said regulatory sequences are preferably promoters or terminators, in particular a transcription initiation start site, a ribosome binding site, an RNA processing signal, a transcription termination site and/or a polyadenylation signal. The nucleic acid molecule is under the control of a suitable promoter and/or a terminator, for example. Suitable promoters can be promoters that are constitutively induced (e.g. the 35S promoter of the cauliflower mosaic virus (Odell et al., *Nature* 313 (1985), 810-812); pathogen-inducible promoters are particularly suitable (e.g. the PRI promoter of parsley (Rushton et al., *EMBO J.* 15 (1996), 5690-5700). Particularly suitable pathogen-inducible promoters are synthetic or chimeric promoters, which do not occur in nature, are composed of multiple elements and contain a minimal promoter, and also comprise at least one cis-regulatory element upstream of the minimal promoter, which serves as a binding site for special transcription factors. Chimeric promoters are designed according to the desired requirements and are induced or repressed by different factors. Examples of such promoters can be found in WO 00/29592, WO 2007/147395 and WO 2013/091612. One example of a suitable terminator is the nos terminator (Depicker et al., *J. Mol. Appl. Genet.* 1 (1982), 561-573). Because direct detection via the expression of the gene tends to be rather difficult, the vectors typically additionally contain indicator/reporter genes or resistance genes for detecting the transmission of the desired vector or DNA molecule/nucleic acid molecule and for selecting the individuals that contain them. Because the nucleic acid molecule according to the invention itself encodes a polypeptide which, with the previously mentioned mutations, represents the protein that imparts resistance to rhizomania, the provision of a further resistance gene for expression in plant cells is not essential. It is preferably provided, however, in order to make quick selection possible.

Examples of indicator/reporter genes are, for example, the luciferase gene and the gene encoding green fluorescent protein (GFP). These also make investigations regarding the activity and/or regulation of a promoter of the gene possible. Examples of resistance genes, in particular for plant transformations, are the neomycin phosphotransferase gene, the hygromycin phosphotransferase gene or the gene encoding phosphinothricin acetyltransferase. However, this does not exclude other indictor/reporter genes or resistance genes known to the person skilled in the art. In a preferred embodiment, the vector is a plant vector.

In a further aspect, the present invention relates to host cells comprising the vectors recombinant DNA molecules and/or nucleic acid molecules according to the invention. A host cell in the sense of the invention can be a prokaryotic (e.g. bacterial) or eukaryotic cell (e.g. a plant cell or a yeast cell). The host cell is preferably an *agrobacterium* such as *Agrobacterium tumefaciens* or *Agrobacterium rhizogenes* or a plant cell.

Numerous methods, such as conjugation or electroporation, are known to a person skilled in the art by means of which he can introduce the nucleic acid molecule according to the invention, the recombinant DNA molecule and/or the vector of the present invention into an *agrobacterium*, as well as methods, such as diverse transformation methods (biolistic transformation, *agrobacterium*-mediated transformation), by means of which he can introduce the nucleic acid molecule according to the invention, the DNA molecule and/or the vector of the present invention into a plant cell (Sambrook et al., *Molecular Cloning: A Laboratory Manual* 3$^{rd}$ Ed. Cold Spring Harbor Laboratory Press, Cold Spring Harbor, N.Y., 2001).

The present invention further preferably relates to a transgenic plant cell, which comprises the nucleic acid molecule or DNA molecule according to the invention as a transgene or the vector of the present invention. Such a transgenic plant cell is, for example, a plant cell that is transformed, preferably in a stable manner, with the nucleic acid molecule according to the invention, the DNA molecule or with the vector of the present invention. In a preferred embodiment of the transgenic plant cell, the nucleic acid molecule is operatively linked to one or more regulatory sequences, which allow the transcription and optionally the expression in the plant cell. The overall construct consisting of the nucleic acid molecule according to the invention and the regulatory sequence(s) then constitutes the transgene. Such regulatory sequences are, for example, a promoter, an enhancer or a terminator. Numerous functional promoters, enhancers and terminators that can be used in plants are known to the person skilled in the art.

A transgenic plant cell according to the present invention, in particular a cell of a plant of the genus *Beta*, preferably exhibits a higher resistance to a pathogen, in particular BNYVV, than a corresponding non-transformed plant cell (the plant cell without the transgene). In plants of the genus *Beta*, the level of resistance, for example to BNYVV, can be qualitatively defined by determining rating scores (rating score schemes for plants of the genus *Beta* are known from the state of the art, for example for sugar beets; see Mechelke (1997) *Probleme in der Rizomaniaresistenzzüchtung* [Problems in rhizomania-resistance breeding], *Vorträge für Pflanzenzüchtung* [Lectures for Plant Breeding], *Resistenzzüchtung bei Zuckerrüben* [Resistance breeding in sugar beets], Gesellschaft für Pflanzenzüchtung e.V. [Society for Plant Breeding], 113-123). Higher resistance is manifested in an improvement of the resistance by at least one rating score, by at least two rating scores, or by at least three or more rating scores. The present invention further also relates to a method for producing a transgenic plant cell of the present invention, which comprises a step of introducing the nucleic acid molecule according to the invention, DNA molecule or the vector of the present invention into a plant cell. The introduction can, for example, take place by transformation, preferably by stable transformation. The suitable introduction techniques, such as biolistic transformation, *agrobacterium*-mediated transformation or electroporation, are known to the person skilled in the art (Sambrook et al., *Molecular Cloning: A Laboratory Manual* 3$^{rd}$ Ed. Cold Spring Harbor Laboratory Press, Cold Spring Harbor, N.Y., 2001).

In a further aspect, the present invention relates to a transgenic plant and parts thereof, comprising a transgenic plant cell as described above. A part can be a cell, a tissue, an organ or a combination of multiple cells, tissues or organs. A combination of several organs is, for example, a flower or a seed. In a particular embodiment, the invention relates to a seed from the transgenic plant, wherein the seed comprises the nucleic acid molecule according to the invention as a transgene. A transgenic plant of the present invention, in particular a plant of the genus *Beta*, preferably exhibits a higher resistance to a pathogen, in particular BNYVV, than a corresponding non-transformed plant (plant without the transgene). In plants of the genus *Beta*, the level of resistance, for example to BNYVV, can be defined qualitatively by determining rating scores (rating score schemes for plants of the genus *Beta* are known from the state of the art, for example for sugar beets; see Mechelke (1997) *Probleme in der Rizomaniaresistenzzüchtung, Vorträge für Pflanzenzüchtung, Resistenzzüchtung bei Zuckerrüben*, Gesellschaft für Pflanzenzüchtung e.V., 113-123). Higher resistance is manifested in an improvement of the resistance by at least one rating score, by at least two rating scores, or by at least three or more rating scores. The invention further provides a method for producing a transgenic plant, which comprises a step of introducing the nucleic acid molecule according to the invention or the vector of the present invention into a plant cell and optionally a step of selecting a transgenic plant cell. Such a method for producing a transgenic plant is additionally characterized by a subsequent step, which includes the regeneration of the transgenic plant from the transgenic plant cell produced in the first step. Methods for regeneration are known to the person skilled in the art from the state of the art.

In a further aspect, the present invention also relates to a method for imparting or increasing a resistance to a pathogen, in particular BNYVV, in a plant, preferably a plant of the genus *Beta*, which includes a step of transforming a plant cell with the nucleic acid molecule according to the invention or the vector of the present invention. Alternatively, as described above, a WB-resistant genotype can be produced from a WB-sensitive genotype by means of random or targeted mutagenesis of the present endogenous wb-s gene.

The wb gene can, for example, be modified via gene mutation by means of TALE nucleases (TALENs) or zinc-finger nucleases (ZFNs) as well as with CRISPR/Cas systems, examples of which are described in WO 2014/144155 A1 (Engineering plant genomes using CRISPR/Cas Systems) and in Osakabe & Osakabe, *Plant Cell Physiol.* 56 (2015), 389-400, among others. This can also be achieved by using the method referred to as TILLING (Targeted Induced Local Lesions in Genomes), wherein, as described in the German patent application DE 10 2013 101 617 for example, point mutations are induced in the wild type gene and plants having a suitable, i.e. resistance-imparting, mutation, such as a barley that is resistant to yellow mosaic virus, are subsequently selected; see DE 10 2013 101 617 on pages 4, 8 and 12 in paragraphs [0014], [0026] and [0038]. The TILLING method is also described in detail in the publication by Henikoff et al. (Henikoff et al, *Plant Physiol.* 135, 2004, 630-636).

Said method preferably leads to an improvement of the resistance by at least one rating score, particularly preferably to an improvement of the resistance by at least two, three or more rating scores. Rating score schemes for plants of the genus *Beta* are known from the state of the art, for example for sugar beets Mechelke (1997). After the mutagenization of the plant cells and the subsequently regeneration of plants from the mutagenized plant cells, or the mutagenization of plants, the plants can then be identified, which, in an endogenous nucleic acid molecule, preferably having the nucleotide sequence that comprises or includes the sequence as per SEQ ID NO: 1 or that hybridizes with the complementary sequence to SEQ ID NO: 1 under stringent conditions, comprise the one or more mutations as defined above.

In a further aspect, the present invention relates to a BNYVV-resistant plant of the genus *Beta* or a part thereof, in which the nucleic acid molecule according to the invention is endogenously present, or in which one or more of the above-defined mutations has been introduced into an endogenous nucleic acid molecule, otherwise correlated with the WB-sensitive genotype, wherein the plant or a part thereof does not belong to the species *Beta vulgaris* subsp. *maritima*. In one embodiment, the plant according to the invention is a hybrid plant or a double-haploid plant. In a further embodiment of the plant according to the invention, the nucleic acid molecule or the one or more mutations are heterozygous or homozygous as defined above. In the case of a hybrid plant, for example, the nucleic acid molecule or the one or more mutations can also be hemizygous.

In a further embodiment, the plant of the present invention additionally transgenically or endogenously comprises a second nucleic acid molecule at another or further position in the genome, which encodes a polypeptide that is capable of imparting a resistance to BNYVV in said plant, in which the polypeptide is expressed as a result of the transcription of the second nucleic acid molecule. Another or further position in the genome can mean that the second nucleotide molecule is located outside the chromosomal interval of chromosome III from s3e4516s05 to s3e5918s01. The RZ3 gene described in the international application WO 2014/202044 A1, for example, can, if not already present in the starting genotype, be introduced into the wb-R plant of the present invention by means of crossbreeding or transformation. Therefore, in a particularly preferred embodiment of the present invention, wb-R/RZ-3-R plants are provided, which are preferably homozygous for one and particularly preferably homozygous for both resistance genes. In light of the foregoing, it goes without saying that, due to the provision of the sequence information for the wb-R gene in the present application and the sequence information for the RZ-3 gene described in the cited WO 2014/202044 A1, for example, such double-resistant plants can for the first time be obtained solely on the basis of crossbreeding and marker-supported selection; there is consequently no need for genetic engineering.

The present invention correspondingly also relates to a method for identifying a plant of the genus *Beta* that is resistant to the pathogen BNYVV, characterized in that the method comprises the following step
(i) detecting the presence and/or expression of a WB resistance-imparting nucleic acid molecule according to the invention in the plant or in a sample thereof; and/or
(ii) detecting at least one marker locus in the nucleotide sequence of the WB resistance-imparting nucleic acid molecule according to the invention or the immediate vicinity, preferably on chromosome III; and/or
(iii) detecting at least two marker loci on chromosome III in the plant, wherein at least one marker locus is located on or within the chromosomal interval from s3e4516s05 to the WB resistance-imparting nucleic acid molecule according to the invention and at least one marker locus is located on or within the chromosomal interval from said nucleic acid molecule to s3e5918s01; as well as optionally
(iv) selecting the BNYVV-resistant plant,
wherein the method is preferably additionally characterized in that the at least one marker locus comprises one or more of the above-defined mutations. In a further embodiment, the method additionally comprises the corresponding detection of a further resistance genotype, particularly preferably the RZ-3 gene as described in WO 2014/202044 A1.

The method advantageously comprises the detection of at least one polymorphism that leads to an amino acid substitution with respect to the amino acid sequence shown in FIG. 1B (SEQ ID NO: 2), preferably at one of the locations highlighted on the amino acid sequence shown in FIG. 1D (SEQ ID NO: 4) (see also the FIGURE legend accompanying FIG. 1) with the polymorphisms highlighted in FIG. 1C (SEQ ID NO: 3), using molecular markers that identify the polymorphisms, in particular diagnostic polymorphisms. This detection preferably takes place using at least one molecular marker per polymorphism, in particular per diagnostic polymorphism. The person skilled in the art knows which marker techniques are to be used to detect a corresponding polymorphism and how to build molecular markers for this purpose. The present invention further includes molecular markers that describe or detect a polymorphism according to FIG. 1C or D, and also the use of a molecular marker for detecting a polymorphism according to FIGS. 1C and/or D. The above identification methods furthermore also represent methods for selecting a plant that has a resistance to BNYVV. The selection method comprises a final step of selecting a resistant plant.

Genomic DNA sequence sections upstream of and adjoining the wb-R gene (such as SEQ ID NO: 3) and genomic DNA sequence sections downstream of and adjoining the wb-R gene, which are located in the immediate vicinity, preferably on chromosome III, and are therefore closely coupled to the wb-R gene, can furthermore be used as DNA regions for developing diagnostic markers for wb-R. The present invention therefore relates to a method for selecting a plant that has a resistance to BNYVV. The method for selection comprises the use of a molecular marker on a DNA sequence as per SEQ ID NO: 3 and/or on a DNA sequence that are located in the immediate vicinity, preferably on chromosome III. Like the markers s3e4516s05 and s3e5918s01 described in the examples, the markers located in the immediate vicinity preferably lie within a range of 0.11 cM, which corresponds to a physical length of the wb-R gene of about 100,000 bp, and show a comparable diagnostic value (DW) such as (a) s3e4516s05_cyt/DW=0.89; left flanking and (b) s3e5918s01_ade/DW=0.91; right flanking. The method further typically includes a final step of selecting a resistant plant. The person skilled in the art knows how to develop and use markers on the basis of the disclosed sequence information.

The present invention thus also relates to a plant, advantageously in particular a BNYVV-resistant plant or a part thereof, which has been identified and optionally selected using a method as described above. The present invention in particular relates to a population of plants including plants, which can be obtained according to any one of the above-described methods according to the invention and are preferably resistant to rhizomania or BNYVV infestation, and are characterized by the presence of a nucleic acid molecule according to the invention. The population preferably includes at least 10, preferably 50, more preferably 100, particularly preferably 500 and, in particular in agricultural cultivation, preferably at least 1000 plants. The proportion of plants in the population that do not carry the nucleic acid molecule according to the invention and/or are susceptible to rhizomania is preferably less than 25%, preferably less than 20%, more preferably less than 15%, even more preferably 10%, and particularly preferably less than 5%, 4%, 3%, 2%, 1% or 0.5%, if present at all.

The use of the present invention furthermore makes it possible to achieve the following advantages for the breeding and the development of new resistant plant lines of the genus *Beta*: sequence information and the identified polymorphisms, which allow a differentiation between resistant wb-R-and susceptible wb-s alleles of the disclosed gene, make the development of markers directly in the gene possible, which, in particular with respect to the development of optimized elite lines without linkage drag, represents a substantial benefit for plant breeders. The knowledge of the sequential structure can also be used to identify other new resistance genes, in particular against rhizomania, which are, for example, in part homologous or orthologous.

The use of the resistant gene allele in cis- or trans-genetic approaches disclosed here opens up the possibility of developing new resistant varieties of the genus Beta, which, based on the dose effect, have a higher resistance or in which, by stacking the disclosed gene with other resistance genes, in particular with the RZ-3 gene, a break in the resistance can be avoided and the resistance manifestation can be optimized. Modifications of the gene by means of TILLING or targeted genome engineering for the development of new resistance alleles are possible as well.

The present invention further relates to the use of the identified resistant wb-R gene allele in a genetic or molecular stack with other genetic elements that can impart agronomically advantageous properties in a plant. The economic value of crop plants can consequently be increased significantly, for example by increasing the yield performance or by developing new cultivation areas for a plant that were previously not accessible for the cultivation of said plant, among other things due to biotic factors such as high pathogen pressure or abiotic factors such as aridity. The present invention relates in particular to the use of the identified resistant wb-R gene allele in methods for controlling infestation with the pathogen beet necrotic yellow vein virus (BNYVV) in the agricultural or horticultural cultivation of plants of the genus Beta, for example comprising the identification and selection of plants of the genus Beta with the aid of one of the above-described methods, and the cultivation of the plants selected in this way or the progeny thereof.

An agronomically advantageous property is, for example, a tolerance to an herbicide such as glyphosate, glufosinate or ALS inhibitors. Numerous further herbicides and their applicability are known to the person skilled in the art from the state of the art. He can refer back to the state of the art to obtain knowledge about which genetic elements are to be used in what manner to implement a corresponding tolerance in plants. Another example of an agronomically advantageous property is an additional pathogen resistance, wherein pathogens can be insects, viruses, nematodes, bacteria or fungi, for example. Because genetic elements can have effects that are mutually supplementary, a broad pathogen defense for a plant, for example, can be achieved by combining different pathogen resistances/tolerances. For this purpose, numerous resistance genes, for example, are known to the person skilled in the art as genetic elements. A further example of an agronomically advantageous property is a cold or frost tolerance. Plants that have this property could be sowed earlier in the year or could remain in the field longer, for example even during periods of frost, which can lead to increased yields, for example. Here too, the person skilled in the art can refer back to the state of the art to find suitable genetic elements. Other examples of agronomically advantageous properties are water utilization efficiency, nitrogen utilization efficiency and yield. Genetic elements that can be used to impart such properties can be found in the state of the art.

Numerous modifications for pathogen defense are also known to the person skilled in the art. In addition to the frequently described families of R-genes, the Avr/R approach, Avr gene complementation (WO 2013/127379), the autoactivation of an R-gene (WO 2006/128444), the HIGS (host-induced gene silencing) approach (e.g. WO2013/050024) or the VIGS (virus-induced gene silencing) approach could advantageously be used. In particular the autoactivation of an R-gene could be significant for the present invention. A nucleic acid that encodes for an autoactivated resistance protein to produce a resistance to pathogens in plants is to be created for this purpose. Said nucleic acid then comprises only a limited portion of an NBS-LRR resistance gene, such as the wb-R gene, which extends from the 5'-end of the encoding region of the NBS-LRR resistance gene downstream to the start of the NBS domain of the NBS-LRR resistance gene, wherein the NBS-LRR-resistance gene is not a TIR-NBS-LRR-resistance gene.

The invention further includes the use of the resistant wb-R gene allele, identified by means of an above-described method, for combination with an above-mentioned modification or with an above-described genetic element that can impart one or more agronomically advantageous properties in a plant.

In addition to the plant according to the invention, the present invention also relates to seeds or progeny, or organs, plant parts, tissue or cells thereof in the production of products typically made from renewable raw materials, such as foodstuffs and animal feed, preferably sugar or syrup (molasses), wherein the molasses is also used for industrial applications, for example for alcohol extraction or as a culture medium for the production of biotechnological products, in the production of materials or substances for the chemical industry, e.g. fine chemicals, pharmaceuticals or precursors thereof, diagnostics, cosmetics, bioethanol or biogas. An example of the use of sugar beets as a biogenic raw material in biogas plants is described in the application DE 10 2012 022 178 A1, see e.g. paragraph 10.

The following examples explain the invention, however without restricting the subject matter of the invention. Unless otherwise stated, standard molecular-biological methods were used, see for example, (Sambrook et al., *Molecular Cloning: A Laboratory Manual* $3^{rd}$ Ed. Cold Spring Harbor Laboratory Press, Cold Spring Harbor, N.Y., 2001, Fritsch et al., Cold Spring Harbor Laboratory Press: 1989; Mayer et al., *Immunochemical Methods in Cell and Molecular Biology*, eds., Academic Press, London, 1987) and Weir et al., *Handbook of Experimental Immunology*, Volumes I-IV, Blackwell, eds., 1986).

EXAMPLES

Example 1: Identification of a Gene (WB1) Imparting Resistance to Rhizomania (WB) and Associated Sensitive Alleles In a population of sugar beets (*Beta vulgaris* L) with an introgression from an accession of *Beta vulgaris* subsp. *Maritima*, it was possible to detect a gene or genome segment that imparts resistance to rhizomania in this introgression by means of markers having a good diagnostic value (DW), (a) s3e4516s05_cyt/DW=0.89; left flanking and (b) s3e5918s01_ade/DW=0.91; right flanking. However, due to the occurrence of null alleles in different pedigrees, the two markers are not completely diagnostic. The genomic region between s3e4516s05 and s3e5918s01 spans a genetic length of 0.11 cM, which corresponds to a physical length of about 100,000 bp. This sequence region is highly repetitive and exhibits a strong structural variation in different genotypes; it is therefore very difficult to develop additional diagnostic markers. As a result of the lack of knowledge of the genetic structure of the rhizomania resistance-imparting genome segment, the further reduction of the potential negative linkage drag around the causal gene is also only possible to a limited extent.

First experiments to further narrow down the relevant genome segment, and possibly discover a gene imparting the observed resistance or a gene locus responsible for the rhizomania-sensitive property of the plants, were unsuccessful, among other things because the target region is very repetitive and exhibits a strong structural variation (null allele) in many genotypes and additional markers having a high diagnostic value were not available. The expression analysis of candidate genes in the target region initially did not provide any evidence, i.e. a specific response to the rhizomania infection, either. Lastly, the phenotyping of the plants proved to be difficult as well, because, for unknown reasons, the resistance manifestation was not always clear, so that the existence of a multigenic resistance was initially assumed as well, and/or epigenetic effects, that were only able to be ruled out by increasing the number of examined plants with 90-180 descendants and using intensive statistical methods (t-test, power analysis).

In experiments and analyses further conducted using map-based cloning, which included the steps of genetic fine mapping, physical mapping, WHG (whole genome) sequence analysis, assembly of a very large splicing population of more than 2000 F2 descendants, recombinant screening, marker development in the target region, comparative BAC sequencing in resistant (RR) and sensitive/ susceptible (ss) genotypes, bioinformatic analyses, protein predictions, and comparison of the proteins, it was then possible to determine that a NB-ARC (NBS-LRR) gene is responsible for the observed rhizomania resistance. This NBS-LRR gene was identified by means of intensive fine mapping, whereby, due to the sequence complexity, the assembling of the RR and ss sequences was difficult. Only by analyzing the progeny of the 4 most closely recombinant plants (2 direct recombinants to the left and two direct recombinants to the right around the gene) was it possible to precisely identify the NBS-LRR gene. The sequence of the NBS-LRR gene of the resistant genotype is shown in SEQ ID NO: 3 and the associated gene or genotype is referred to as "wb-R" for "rhizomania resistance". A total of 17 "non-synonymous" single nucleotide polymorphisms (SNPs) were found in the NBS-LRR gene (polymorphisms that lead to an amino acid substitution in the protein). Based on sequence data consisting of sensitive and resistant genotypes, five amino acid substitutions were found to be completely diagnostic:

K307Q, "C" instead of "A" in the genomic sequence at position 919 in the resistant genotype, which replaces the encoded lysine (K) at position 307 of the susceptible gene with a glutamine (Q), Q437R, "G" instead of "A" in the genomic sequence at position 1310 in the resistant genotype, which replaces the encoded glutamine (Q) at position 437 of the susceptible gene with an arginine (R), R566H, "A" instead of "G" in the genomic sequence at position 1697 in the resistant genotype, which replaces the encoded arginine (R) at position 566 of the susceptible gene with a histidine (H), Q731K, "A" instead of "C" in the genomic sequence at position 2191 in the resistant genotype, which replaces the encoded glutamine (Q) at position 731 of the susceptible gene with a lysine (K), and P831S, "T" instead of "C" in the genomic sequence at position 2491 in the resistant genotype, which represents the encoded proline (P) at position 831 of the susceptible gene with a serine (S); see FIG. 1. Based on the recombination sites, one of the two or both amino acid substitutions K307Q or Q437R can be regarded as causative for the imparting of the resistance. The corresponding gene sequences or genotypes that are correlated with the phenotype that is sensitive to rhizomania are also referred to as "wb-s," which stands for "rhizomania-sensitive."

Example 2: Validation of the Wb-R Gene Using an RNAi Approach

In addition to the above-described verification of the gene using close recombinants, the resistance effect of the gene can be demonstrated with the aid of RNA interference as further evidence; see, for example, the verification of the RZ-3 gene described in the examples of the international application WO 2014/202044 A1 or the verification of the vi1 gene described in the examples of the international application WO 2011/032537 A1. To do so, a resistant standard sugar beet genotype is transformed with a DNA construct which encodes a double-stranded hairpin RNA. This dsRNA is capable of effecting post-transcriptional gene silencing, which would reduce or switch off the action of the resistant wb-R gene allele. As a result, the previously resistant sugar beet genotype should become sensitive to rhizomania.

In order to provide a suitable DNA construct, a defined target sequence region of the resistant wb-R gene allele having a length of 400-500 base pairs, for example, is preferably selected from a region of the encoding sequence that is specific for the resistant wb-R gene allele, amplified by PCR and cloned in both sense direction and antisense direction into the vector pZFN, which is suitable for the synthesis of hairpin structures (see FIG. 6 of the international application WO 2014/202044 A1). This vector comprises a dual CaMV 35S promoter, a multiple cloning site, an intron from the AtAAP6 gene, which encodes for an amino acid permease in *Arabidopsis thaliana*, a further multiple cloning site as well as a nos terminator. The transformation of the sugar beets with the provided vector takes place according to the protocol of Lindsey & Gallois, *J. Exp. Bot.* 41 (1990), 529-536, using the antibiotic kanamycin as a selection marker. After several selection steps, the successful transformation is verified on transgenic shoots using PCR via the detection of the presence of the nptII gene, the AAP6 intron and the two t-DNA border sequences (LB/RB) and the absence of vir. Positive shoots are clonally propagated in vitro to 30 shoots at a time, rooted and transferred to soil in a greenhouse. About 2 weeks later, the transgenic sugar beet plants are transplanted into rhizomania contaminated soil, in which they are cultivated for 8 to 10 weeks. As a control, non-transformed plants of the same resistant genetic standard transformation background are grown under the same conditions. In order to detect the manifestation of rhizomania, the roots of the sugar beet plants are harvested and the BNYVV infestation is quantified by means of an ELISA test, whereby a low ELISA value indicates a resistance and a high value indicates a sensitivity (Mechelke 1997, above; Clark & Adams, *J. Gen. Virol.* 34 (1977), 475-483). As expected, with an average value of 3-4, the ELISA value of the transformed sugar beets is significantly higher than the ELISA value of the still resistant control having an average value of 1-2 and is comparable to the sensitive standard. The results of the ELISA test can then be used to show that, as a result of the specific gene silencing of the resistant wb-R allele in the transformation background, a previously resistant plant becomes sensitive to BNYVV. The wb-R gene of the present invention can consequently be unequivocally verified as the resistance gene.

The validation of the gene function can also be carried out via the complementation of a WB-sensitive plant, in particular sugar beet, with a wb-R gene according to the invention, for example in which a plant expression vector containing a nucleic acid molecule having the nucleotide sequence of SEQ ID NO: 3 or an equivalent nucleotide sequence that encodes a polypeptide having an amino acid sequence of SEQ ID NO: 4 is transformed in a sensitive genotype; in each case under the control of a constitutive promoter. The pZFN vector described above and the techniques mentioned, or even those described above in the general description, can usually be used for the transformation.

SUMMARY

The provision of the wb-R gene according to the invention makes a more efficient breeding against rhizomania and/or the development of new resistant lines possible. The wb-R gene and embodiments of the present invention described above provide additional applications, for example the use of the resistant gene allele in cis- or trans-genetic approaches with the objective of developing new resistant varieties, "gene stacking" i.e. increasing the resistance on the basis of the dose effect, modification of the gene by means of TILLING or targeted genome engineering/gene editing to develop new resistance alleles, and the determination of the interactions between wb-R and other rhizomania resistance genes to develop varieties having an optimum resistance manifestation.

The invention claimed is:

1. A method for controlling infestation with the pathogen beet necrotic yellow vein virus (BNYVV) in the agricultural or horticultural cultivation of plants of the genus *Beta*, comprising:

detecting the presence and/or expression of a nucleic acid molecule that encodes a polypeptide having the amino acid sequence of SEQ ID NO: 2 in which at least one amino acid substitution is present as a result of one or more mutations of the nucleotide sequence in the plant or in a sample thereof;

(ii) selecting the BNYVV-resistant plant; and (iii) cultivating the selected plant or the progeny thereof;

wherein the amino acid substitution results in one or more selected from the group consisting of: a substitution of glutamine (Q) at position 307; and arginine (R) at position 437.

2. The method of claim 1, wherein the selected plant is a *Beta vulgaris* plant.

3. The method of claim 1, wherein the *Beta vulgaris* plant is selected from the group consisting of: *Beta vulgaris* ssp. *vulgaris* var. *vulgaris* (chard), *Beta vulgaris* ssp. *vulgaris* var. *conditiva* (red beet/beetroot), *Beta vulgaris* ssp. *vulgaris* var. *crassa/alba* (fodder beet).

4. The method of claim 1, wherein the selected plant is a *Beta vulgaris* ssp. *vulgaris* var. *altissima* plant.

\* \* \* \* \*